US011162946B2

(12) United States Patent
Young et al.

(10) Patent No.: US 11,162,946 B2
(45) Date of Patent: Nov. 2, 2021

(54) METHODS, DEVICES, AND SYSTEMS FOR SAMPLE ANALYSIS

(71) Applicant: Theranos, Inc., Palo Alto, CA (US)

(72) Inventors: Daniel Young, Palo Alto, CA (US); Elizabeth A. Holmes, Palo Alto, CA (US)

(73) Assignee: Labrador Diagnostics LLC, Wilmington, DE (US)

( * ) Notice: Subject to any disclaimer, the term of this patent is extended or adjusted under 35 U.S.C. 154(b) by 436 days.

(21) Appl. No.: 14/854,382

(22) Filed: Sep. 15, 2015

(65) Prior Publication Data

US 2016/0231320 A1  Aug. 11, 2016

Related U.S. Application Data

(63) Continuation of application No. PCT/US2014/032071, filed on Mar. 27, 2014.

(60) Provisional application No. 61/805,900, filed on Mar. 27, 2013.

(51) Int. Cl.
*G01N 33/569* (2006.01)
*C12Q 3/00* (2006.01)
*G01N 33/50* (2006.01)

(52) U.S. Cl.
CPC ......... *G01N 33/56983* (2013.01); *C12Q 3/00* (2013.01); *G01N 33/5094* (2013.01); *G01N 33/56966* (2013.01); *G01N 2333/16* (2013.01); *G01N 2333/70557* (2013.01); *G01N 2333/70596* (2013.01); *G01N 2469/10* (2013.01)

(58) Field of Classification Search
None
See application file for complete search history.

(56) References Cited

U.S. PATENT DOCUMENTS

| | | | |
|---|---|---|---|
| 5,731,156 A | 3/1998 | Golbus | |
| 5,795,784 A * | 8/1998 | Arnquist | G01N 35/0092 422/63 |
| 8,361,737 B2 * | 1/2013 | Monif | C12Q 1/689 435/7.32 |
| 9,702,852 B2 * | 7/2017 | Lowery, Jr. | G01N 27/745 |
| 2002/0028158 A1 * | 3/2002 | Wardlaw | G01N 15/05 422/82.05 |
| 2002/0119447 A1 | 8/2002 | Simons et al. | |
| 2003/0095897 A1 * | 5/2003 | Grate | B03C 1/00 422/186 |
| 2003/0198998 A1 * | 10/2003 | Uttenthal | C07K 16/18 435/7.1 |
| 2004/0132218 A1 * | 7/2004 | Ho | B01L 3/5025 436/524 |
| 2005/0106642 A1 * | 5/2005 | Lipps | G01N 33/57488 435/7.23 |
| 2005/0112024 A1 * | 5/2005 | Guo | A61B 10/007 422/562 |
| 2005/0227370 A1 * | 10/2005 | Ramel | C12Q 1/00 436/514 |
| 2006/0004526 A1 | 1/2006 | Hadd et al. | |
| 2006/0183217 A1 * | 8/2006 | Yanagida | G01N 1/38 435/287.2 |
| 2006/0292547 A1 | 12/2006 | Pettegrew et al. | |
| 2006/0292647 A1 * | 12/2006 | Green | G01N 33/5695 435/7.32 |
| 2007/0054414 A1 * | 3/2007 | Burgess-Cassler | B01L 3/5023 436/514 |
| 2007/0111225 A1 | 5/2007 | Lambert et al. | |
| 2007/0212721 A1 * | 9/2007 | Fischer | G01N 33/57449 435/6.14 |
| 2008/0124738 A1 * | 5/2008 | Green | C12Q 1/04 435/7.1 |
| 2008/0255705 A1 | 10/2008 | Degeal et al. | |
| 2008/0300789 A1 * | 12/2008 | Fritchie | G01N 35/0092 702/1 |
| 2009/0088336 A1 | 4/2009 | Burd et al. | |
| 2009/0155788 A1 * | 6/2009 | Abbas | C12Q 1/6883 435/6.17 |

(Continued)

FOREIGN PATENT DOCUMENTS

| | | |
|---|---|---|
| CN | 102768271 A | 11/2012 |
| EP | 0397424 A2 | 11/1990 |

(Continued)

OTHER PUBLICATIONS

International Search Report and Written Opinion dated Jan. 28, 16 for PCT/US2015/035112.
Lehmann H-P et al. HEp2 ANA EIA: A new fully automated assay for the screening of antinuclear antibodies. Israel Medical Association Journal 2000 IL, vol. 2, No. 8, 2000, pp. 646-648.
Steven M. Chan et al. Intensive serial biomarker profiling for the prediction of neutropenic fever in patients with hematologic malignancies undergoing chemotherapy: a pilot study. Hematology Reports, vol. 6, No. 2, Apr. 22, 2014.

(Continued)

*Primary Examiner* — Ann Y Lam

(57) ABSTRACT

Methods, devices, and systems for analyzing biological samples are provided. A biological sample may be analyzed for the presence of an analyte by an initial assay, and the performance of, or method of performance of, a subsequent assay may be contingent upon the results of the initial assay. For example, the following may be contingent on the results of a prior assay: whether or not a subsequent assay is performed; which subsequent assay is performed; the method of performing a subsequent assay; the order of performance of a sequence of subsequent assays; the steps, or order of steps, performed in a subsequent assay; the timing of the performance of a subsequent assay; the choice of a reagent used in a subsequent assay; the detection method used in a subsequent assay; and other particulars of assays may be contingent on the results of a prior assay.

19 Claims, 4 Drawing Sheets

(56) References Cited

U.S. PATENT DOCUMENTS

| | | | | |
|---|---|---|---|---|
| 2010/0009343 | A1* | 1/2010 | Fischer | C12Q 1/6851 435/5 |
| 2010/0113429 | A1* | 5/2010 | White | A61K 31/435 514/221 |
| 2010/0267041 | A1* | 10/2010 | Shuber | G01N 33/68 435/6.14 |
| 2011/0046910 | A1 | 2/2011 | Haas et al. | |
| 2011/0129870 | A1* | 6/2011 | Rising | G01N 21/51 435/30 |
| 2011/0245087 | A1* | 10/2011 | Weiss | C12Q 1/6886 506/7 |
| 2011/0256630 | A1* | 10/2011 | Clinton | G01N 35/028 436/48 |
| 2014/0073043 | A1* | 3/2014 | Holmes | G01N 33/5005 435/287.3 |
| 2014/0170735 | A1* | 6/2014 | Holmes | G01N 21/07 435/287.1 |
| 2014/0287423 | A1* | 9/2014 | Nurse | B01L 3/502707 435/6.12 |

FOREIGN PATENT DOCUMENTS

| | | |
|---|---|---|
| EP | 1887357 B1 | 5/2013 |
| WO | 2006083969 A2 | 8/2006 |
| WO | 2012083250 A2 | 6/2012 |
| WO | 2014127379 A1 | 8/2014 |

OTHER PUBLICATIONS

International Search Report dated Aug. 14, 2014 for PCT/US2014/032071.
Rosner M. et al. Merging high quality biochemical fractionation with a refined flow cytometry approach to monitor nucleocytoplasmic protein expression throughout the unperturbed mammalian cell cycle. Nature protocols, 2013, vol. 8, No. 3 (Published online Feb. 28, 2013): 602-626; doi:10.1038/nprot.2013.011, especially pp. 603-604.
Réunis Laboratoires: "Formulaire de Demande" Jan. 6, 2021.

* cited by examiner

Scatter

1A

CD14- Pac Blue for Monocytes

1B

CD123-PECy5 for Basophils

1C

CD16-PE for Neutrophils

1D

CD45-AF647 for all leukocytes

1E

DRAQ5® as a nuclear stain

1F

4A

4B

4C

4D

4E

4F

METHODS, DEVICES, AND SYSTEMS FOR SAMPLE ANALYSIS

BACKGROUND

Rapid and accurate detection and identification of analytes and pathogens in biological samples is useful in the diagnosis of diseases and disorders in subjects. However, such analysis may be a multi-step process, and it may be advantageous, or may be required, that different assays be performed in sequence. Assay devices and systems may be configured for one, but not all, of the assays required for a complete analysis.

Accordingly, improved methods, devices, and systems for analysis of biological samples are required.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY

Methods, devices, and systems for the analysis of biological samples are provided which may be configured to perform multiple assays on a sample or samples, comprising an initial assay or multiple initial assays, and further comprising a subsequent assay or subsequent assays, the performance of, and/or order of performance of, such subsequent assay or assays being contingent on the results of such initial assay(s). Thus, a subsequent assay or such subsequent assays may be performed in a contingent manner, wherein the performance of a subsequent assay depends on the results of one or more prior assay. In embodiments, whether or not a subsequent assay is performed at all may be contingent on the results of a prior assay. In embodiments, the order of performance of subsequent assays, or of steps in a subsequent assay, may be contingent on the results of a prior assay. In embodiments, the choice of a subsequent assay, from among a plurality of possible subsequent assays, may be contingent on the results of a prior assay. In embodiments, the method of performing a subsequent assay may be contingent on the results of a prior assay. In embodiments, the timing of the performance of a subsequent assay may be contingent on the results of a prior assay. In embodiments, the choice of a reagent used in a subsequent assay may be contingent on the results of a prior assay. In embodiments, the choice of a method of detection used in a subsequent assay may be contingent on the results of a prior assay. In embodiments, the choice of whether or not to use a second biological sample in a subsequent assay may be contingent on the results of a prior assay in which a first biological sample was assayed. In embodiments, the choice of whether or not to obtain a second biological sample may be contingent on the results of a prior assay of a first biological sample. In embodiments, the choice of whether or not to obtain a second biological sample for use in a subsequent assay may be contingent on the results of a prior assay of a first biological sample.

In embodiments, analysis of a biological sample may comprise assaying the sample, or a portion of the sample, for the presence of an analyte. An analyte is the subject of an analysis. An analyte may be a natural constituent of a biological sample, or may be an element, compound, material, or cell not normally found in a biological sample that may be the subject of analysis. An analyte may comprise a chemical compound, e.g., a small molecule, a protein, a nucleic acid, or other compound, present in the sample. An analyte may comprise a physical or chemical characteristic of a sample, or of a portion of the sample. An analyte may comprise a marker or physical or chemical characteristic of a cell or virus in a sample, or in a portion of the sample. An analyte may comprise a cell or virus, or portion thereof, in a sample, or in a portion of the sample.

Accordingly, methods, devices, and systems are disclosed herein. In embodiments, a method of testing a biological sample comprises:

performing an initial assay for the presence of an analyte in said biological sample, whereby an initial result is obtained, wherein said initial assay may provide a negative result indicating that the presence of said analyte is not detected in the biological sample, or may provide a positive result indicating that the presence of the analyte is detected in the biological sample; and determining further testing of said biological sample contingent on said initial result, wherein if the initial result is negative, then no further assay is performed on said biological sample; and wherein if the initial result is positive, then a further assay is performed on said biological sample.

In embodiments, a method of testing a biological sample comprises:

performing an initial assay in a device for an analyte in said biological sample, whereby an initial result is obtained, wherein said initial assay may provide a negative result indicating that the presence of said analyte is not detected, or is detected at a normal level, in the biological sample, or may provide a positive result indicating that the presence of the analyte is detected, or is detected at an abnormal level, in the biological sample; and determining further testing of said biological sample contingent on said initial result, wherein if the initial result is negative, then no further assay is performed on said biological sample; and wherein if the initial result is positive, then a further assay is performed in said device on said biological sample.

In embodiments, such further assay may be a type of assay selected from the group consisting of antibody-based assays, nucleic acid assays, general chemistry assays, and cytometric assays. In embodiments, the further assay may comprise an assay of a different type than the initial assay type. In embodiments, such further assays may comprise assays that are more sensitive for the detection of said analyte than said initial assay. In embodiments, the analyte to be detected by such further assays may comprise a different analyte than the analyte to be detected by said initial assay.

In embodiments, such an initial assay may comprise the use of a detector to obtain said initial result, wherein said detector is selected from an optical detector, a pH detector, an electrochemical detector, a temperature sensor, an ion-sensitive electrode, a radiation detector, and other detectors. In embodiments, such a further assay may comprise the use of a detector to obtain a further result, wherein said detector is selected from an optical detector, a pH detector, an electrochemical detector, a temperature sensor, an ion-sensitive electrode, a radiation detector, and other detectors.

Methods disclosed herein comprise protocols for performance of a sequence of assays. In embodiments, protocols may include contingent assays, whose performance is dependent on the results of prior assays, wherein a result of a first assay, if it meets a criterion, triggers, alters, or prevents the performance of a subsequent assay. In embodiments, such a subsequent assay may not be performed in the absence of prior results which meet the criterion. In embodiments, the performance of a subsequent assay may be contingent on two, or three, or more criteria. Protocols include contingent sequences of assays, where the performance of a subsequent assay is determined by the outcome of an assay performed prior to the performance of the subsequent assay. In embodiments, a protocol including one or more contingent sequences of assays may be requested at the time the assays are ordered. In embodiments, a protocol including one or more contingent sequences of assays may be determined at the time the assays are ordered. In embodiments, a protocol including one or more contingent sequences of assays may be requested at the time the assays are ordered, and the particulars of the sequence, and of the contingent steps, may be determined at a time after the time the assays are ordered.

In embodiments, a protocol including one or more assays, whose performance or sequence of performance is contingent on the result of an initial assay, may include instructions, or a protocol, for the acquisition of a biological sample. In embodiments, such a protocol may direct or require that a biological sample of sufficient volume or amount be acquired in order to provide sufficient biological sample for the performance of a contingent assay, if the contingent assay is needed. In embodiments, such a protocol may direct or require that a biological sample be divided into aliquots for the performance of a contingent assay, if the contingent assay is needed. In embodiments, such a protocol may direct or require that a biological sample be diluted, in order to provide sufficient biological sample for the performance of a contingent assay, if the contingent assay is needed. In embodiments, such a protocol may direct or require that a biological sample, or portion or dilution thereof, be retained for use in the performance of a contingent assay, if the contingent assay is needed.

Optionally, it should be understood that embodiments herein do not exclude protocols wherein if a contingent assay is indicated on the test order or other instruction, the contingent assay is automatically run, regardless of the results from any initial assay. Such contingent assay(s) may be run concurrently with or even before results are available from any initial assay(s). Although such alternative protocols may result in additional usage of reagent(s), diluent(s), and/or other materials, the workflow of parallel, concurrent, or continuous processing may be beneficial in some situations, such as but not limited excess system availability while processing the initial assays or waiting for initial assays to complete.

In embodiments, an initial assay may comprise a less sensitive assay, and a subsequent assay may comprise a more sensitive assay; in embodiments, performance of a subsequent assay may be contingent on the results of the initial assay. For example, an initial assay may comprise a nucleic acid assay performed under a first condition, and a subsequent assay may comprise a nucleic acid assay performed under a second condition, where the second condition comprises more stringent nucleic acid assay conditions than the first condition (e.g., the second condition comprises a higher temperature than the first condition, or the second condition comprises a lower ionic strength than the first condition, or the second condition comprises a denaturing agent (such as formamide) not present, or present at a lower concentration, in the first condition). In embodiments, an initial assay that comprises a nucleic acid assay may be performed under moderately stringent conditions, and a subsequent assay may comprise a nucleic acid assay performed under high stringent conditions.

In embodiments, an initial assay may comprise a first type of assay, and a subsequent assay, contingent on the results of the initial assay may comprise a second type of assay; for example, an initial assay may comprise an antibody-based assay, and a subsequent assay may comprise a nucleic acid assay.

Accordingly, Applicant further discloses methods of testing a biological sample in a device, comprising: performing an initial assay in said device for an analyte in said biological sample, whereby an initial result is obtained, wherein said initial assay may provide a negative result indicating that the presence of said analyte is not detected, or is detected at a normal level, in the biological sample, or may provide a positive result indicating that the presence of the analyte is detected, or is detected at an abnormal level, in the biological sample; performing further testing of said biological sample, wherein a further assay is performed in said device on said biological sample regardless of the results of said initial assay; and reporting the results of said further assay of said biological sample contingent upon the results of said initial assay.

In embodiments, the methods further comprising reporting the results of said initial assay. In embodiments, the results of said further assay are not reported if said initial assay provides a negative result, and wherein the results of said further assay are reported if said initial assay provides a positive result. In embodiments, the results of said further assay are not reported if said initial assay provides a positive result, and wherein the results of said further assay are reported if said initial assay provides a negative result.

In embodiments, the further assay is an assay for the same analyte as said initial assay, and the further assay is a more sensitive assay than said initial assay.

In embodiments, the biological sample upon which the further assay is performed is obtained before the results of said initial assay are obtained. In embodiments, the initial assay and the further assay are performed on portions of the same biological sample. In embodiments, at least one of said portions of said biological sample is a diluted portion of the biological sample. In embodiments, the further assay comprises an assay of a type selected from the group of assay types consisting of antibody-based assays, nucleic acid assays, general chemistry assays, and cytometric assays. In embodiments, the further assay comprises a different type of assay than the initial assay. In embodiments, the analyte to be detected by said further assay comprises a different analyte than the analyte detected by said initial assay. In embodiments, the initial assay comprises measurement of an analyte, and said further assay comprises a cytometric assay.

The methods, compositions, devices, and systems provide rapid tests, which require only small biological samples, and thus provide advantages over other methods, compositions, assays, devices, and systems. Devices and systems disclosed herein are configured to perform such rapid assays which require only small amounts of sample, such as only small amounts of sample, urine, sputum, tears, material obtained from a nasal swab, throat swab, cheek swab, or other biological sample. Accordingly, the methods, devices, and systems provide rapid tests, which require only small biological samples, and thus provide advantages over other methods, compositions, assays, devices, and systems.

In embodiments, a biological sample may comprise a sample selected from blood, serum, plasma, a throat swab, a nasal swab, a nasopharyngeal wash, saliva, urine, gastric fluid, cerebrospinal fluid, tears, stool, mucus, sweat, earwax, oil, a glandular secretion, semen, vaginal fluid, interstitial fluids derived from tumorous tissue, ocular fluids, breath, hair, finger nails, skin, biopsy tissue, placental fluid, amniotic fluid, cord blood, lymphatic fluids, cavity fluids, sputum, pus, microbiota, meconium, breast milk, and other secretions or excretions.

In embodiments, such an initial assay and such a further assay may be performed on different biological samples. In embodiments, the biological sample upon which the further assay is performed may be obtained before the results of said initial assay are obtained. In embodiments, the biological sample upon which the further assay may be performed is obtained after the results of said initial assay are obtained.

Accordingly, Applicant discloses herein methods in which a further assay is performed within a short amount of time from the time at which the biological sample tested by the further assay was accepted within the device. In embodiments, the initial assay and the further assay are each performed on at least a portion of the same biological sample; in such embodiments, the further assay is performed within a short amount of time from the time at which an initial biological sample was accepted within the device.

In embodiments, a further assay is performed if an initial assay is performed. In embodiments of methods disclosed herein, if the result of said initial assay performed in a device is positive, then a further assay is performed on a biological sample in the same device within a short amount of time from the time of accepting a sample within said device, wherein said short amount of time is a time prior to the performance of the further assay. In embodiments, the same sample is used for the performance of both the initial assay and the further assay, or portions of the same sample are used for the performance of both the initial assay and the further assay. Such a short amount of time may be, for example, a short amount of time consisting of about 3 hours or less; about 2 hours or less; about 1 hour or less; about 50 minutes or less; about 45 minutes or less; about 40 minutes or less; about 35 minutes or less; about 30 minutes or less; about 25 minutes or less; about 20 minutes or less; about 15 minutes or less; about 10 minutes or less; about 5 minutes or less; about 4 minutes or less; about 3 minutes or less; about 2 minutes or less; and about 1 minute or less.

In embodiments, the biological sample upon which the further assay is performed is obtained after the results of said initial assay are obtained; in such embodiments, the further assay is performed within a short amount of time from the time at which a further biological sample was accepted within the device. Such a further biological sample may be obtained following the time at which an initial biological sample is obtained. In embodiments, a further biological sample is obtained from a subject during a single session in which biological samples are obtained. In embodiments, a further biological sample is obtained from a subject during a second, or subsequent, session following the session during which the initial biological sample was obtained. In embodiments, a second, or subsequent, session may follow the session during which the initial biological sample was obtained by a time period of about 10 minutes or less; or about 20 minutes or less; or about 30 minutes or less; or about 40 minutes or less; or about 50 minutes or less; or about one hour or less; or about two hours or less; or about three hours or less; or other time period.

The assays and methods disclosed herein may be performed on a device, or on a system, for processing a sample. The assays and methods disclosed herein can be readily incorporated into and used in an automated assay device, and in an automated assay system. In embodiments, a device as disclosed herein may be suitable for detection, identification, or measurement of an analyte in a biological sample.

In embodiments, a device for assaying a sample for the presence of analyte in a sample may comprise: a fluid handling system for transporting at least a portion of a biological sample; and a detector effective to detect or measure an analyte. In embodiments, a detector may comprise one or more of an optical detector, a pH sensor, an electrochemical detector, a radiation detector, a temperature sensor, and other sensors. An optical detector may comprise one or more of a camera, a photomultiplier, a photodiode, a spectrophotometer, and other optical elements. In embodiments, a device for assaying a sample for the presence of analyte in a sample may comprise a system for transporting at least a portion of a sample. In embodiments, a device for assaying a sample for the presence of analyte in a sample may comprise a system for transporting a reagent. In embodiments, a system for transporting at least a portion of a sample, or for transporting a reagent, may comprise a fluid handling system. In embodiments, a fluid handling system of a device for assaying a sample for the presence of analyte in a sample may be configured to transport at least a portion of a biological sample and also be configured to transport a reagent. In embodiments, a device for assaying a sample for the presence of analyte in a sample may be configured to dilute at least a portion of a sample with a reagent. In embodiments, a device for assaying a sample for the presence of analyte in a sample may be configured to mix a reagent with at least a portion of a sample.

In embodiments, a device comprising a fluid handling system for transporting at least a portion of a biological sample may comprise a means for contacting a biological sample; or may comprise a means for accepting a biological sample; or may comprise means for storing a biological sample. In embodiments, a biological sample may be provided by a cartridge. In embodiments, a cartridge may hold a container in which a biological sample is contained. A container configured to hold a biological sample may be configured to store a biological sample, and may be configured to allow access to said biological sample by a fluid handling system. Access by a fluid handling system to a biological sample may be effective to allow transport of at least a portion of the biological sample; to allow mixing of the biological sample; to allow addition of a reagent to at least a portion of the biological sample; or to allow division of said biological sample into two or more portions.

In embodiments, systems are provided which include devices configured to detect the presence of an analyte in a biological sample. In embodiments, a device or system may further comprise a communication assembly, which may comprise a display element and/or a communication element effective to report the results of said detection and/or measurement. In embodiments, a communication assembly, such as a display element and/or communication element, may be suitable for two-way communication. In embodiments, a communications assembly may be configured to communicate data obtained from assaying a sample. In embodiments, a device for assaying a sample for the presence of analyte in a sample may comprise other elements and assemblies, including, without limitation, a heating assembly, a cooling assembly, a sonicator, and other elements and assemblies.

For example, systems as disclosed herein may include a communication assembly for transmitting or receiving a protocol based on the analyte to be detected or based on other analytes to be detected by the device or system. In embodiments, an assay protocol may be changed based on results previously obtained from a sample from a subject, or based on results previously obtained from a different sample from the subject. In embodiments, a communication assembly may comprise a channel for communicating information from said device to a computer, said wherein said channel is selected from a computer network, a telephone network, a metal communication link, an optical communication link, and a wireless communication link. In embodiments, systems as disclosed herein may transmit signals to a central location, or to an end user, and may include a communication assembly for transmitting such signals. Systems as disclosed herein may be configured for updating a protocol as needed or on a regular basis.

Accordingly, Applicant discloses devices configured to measure an analyte in a biological sample according to a method disclosed herein. Devices configured to measure analytes in a biological sample according to a method disclosed herein may be configured to measure analytes from a biological sample that comprises no more than about 1000 μL of sample, or no more than about 500 μL of sample, no more than about 250 μL of sample, or no more than about 150 μL of sample, or no more than about 100 μL of sample, or no more than about 50 μL of sample, or, in embodiments, wherein said biological sample comprises no more than about 25 μL of sample, or wherein said biological sample comprises no more than about 10 μL of sample, or wherein said biological sample comprises less than about 10 μL of sample. Such devices may be configured to measure an analyte in a biological sample in less than about one hour, or, in embodiments, in less than about 40 minutes, or in less than about 30 minutes.

Devices disclosed herein may be configured to perform an assay for the measurement of a first analyte and also to perform an assay for the measurement of a second analyte in the biological sample. In embodiments, performance of an assay for the measurement of a second analyte in the biological sample may be contingent on the results of an assay for the measurement of a first analyte in the biological sample. For example, devices disclosed herein may be configured to perform an assay for the measurement of an analyte and also to perform an assay comprising the measurement of a morphological characteristic of a blood cell in the blood sample. Devices disclosed herein may be configured to perform an assay for the measurement of a first analyte and also to perform an assay comprising the measurement of another blood analyte, e.g., a vitamin, a hormone, a drug or metabolite of a drug, or other analyte. Such devices may be configured wherein the assays, or the order of performance of assays, that are performed by said device may be altered by communication with another device.

Applicant also discloses systems comprising a device as disclosed herein. In embodiments, the system comprises a device that is configured to perform an assay for the measurement of a first analyte and also to perform an assay for the measurement of another analyte in the blood sample. In embodiments, the system comprises a device that is configured to perform an assay for the measurement of an analyte and also to perform an assay for the measurement of a morphological characteristic of a blood cell in the blood sample. In embodiments of such a system, assays, or the order of performance of assays, that are performed by said device may be altered by communication with another device.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

DETAILED DESCRIPTION

Figure 1:
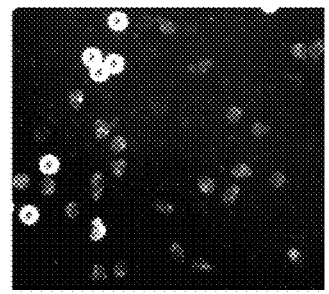
FIG. 1A shows representative images of blood cells from a sample of whole blood, illustrating a light-scattering image.
FIG. 1B shows representative images of blood cells from a sample of whole blood, illustrating an image of cells stained for the monocyte marker CD14 with Pac-Blue.
FIG. 1C shows representative images of blood cells from a sample of whole blood, illustrating an image of cells stained for the basophil marker CD123 with PEcy5.
FIG. 1D shows representative images of blood cells from a sample of whole blood, illustrating an image of cells stained for the neutrophil marker CD16 with PE.
FIG. 1E shows representative images of blood cells from a sample of whole blood, illustrating an image of cells stained for the leukocyte marker CD45 with AF647.
FIG. 1F shows representative images of blood cells from a sample of whole blood, illustrating an image of cells stained with the nuclear marker DRAQ5®.
Figure 1:
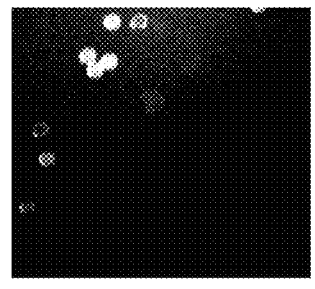
Figure 1:
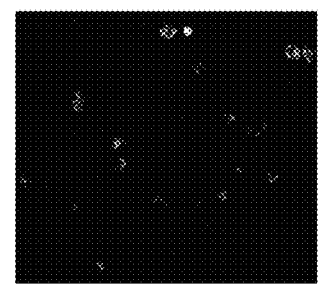
Figure 1:
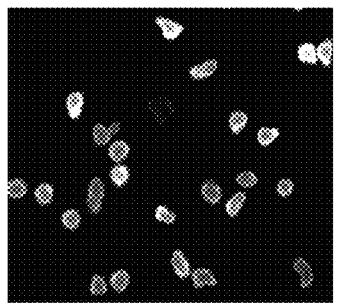
Figure 1:
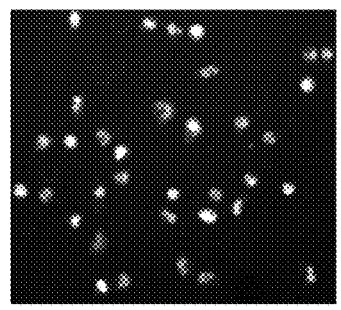
Figure 1:
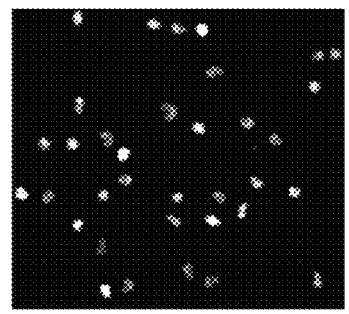

Description and disclosure of examples of reagents, assays, methods, kits, devices, and systems which may use, or be used with, methods, devices, and systems disclosed herein may be found, for example, in U.S. Pat. Nos. 8,088,593; 8,380,541; U.S. patent application Ser. No. 13/769,798, filed Feb. 18, 2013; U.S. patent application Ser. No. 13/769,779, filed Feb. 18, 2013; U.S. patent application Ser. No. 13/769,817, filed Feb. 18, 2013; U.S. patent application Ser.

No. 13/769,818, filed Feb. 18, 2013; U.S. patent application Ser. No. 13/769,820, filed Feb. 18, 2013; U.S. patent application Ser. No. 13/244,947 filed Sep. 26, 2011; PCT/US2012/57155, filed Sep. 25, 2012; U.S. application Ser. No. 13/244,946, filed Sep. 26, 2011; U.S. patent application Ser. No. 13/244,949, filed Sep. 26, 2011; U.S. Patent Application 61/805,900, filed Mar. 27, 2013; and U.S. Application Ser. No. 61/673,245, filed Sep. 26, 2011, the disclosures of which patents and patent applications are all hereby incorporated by reference in their entireties.

Definitions

Before the present methods, devices, and systems are disclosed and described, it is to be understood that the terminology used herein is for the purpose of describing particular embodiments only and is not intended to be limiting. It is also to be understood that the present disclosure provides explanatory and exemplary descriptions and examples, so that, unless otherwise indicated, the devices, systems, and methods disclosed herein are not limited to the specific embodiments described herein.

It must be noted that, as used in the specification and the appended claims, the singular forms "a," "an" and "the" include plural referents unless the context clearly dictates otherwise. Thus, for example, reference to "a salt" refers to a single salt or mixtures of different salts, and the like.

In this specification and in the claims that follow, reference will be made to a number of terms, which shall be defined to have the following meanings:

Acronyms and abbreviations, such as "rpm" (revolutions per minute), "min" (minute), "sec" (second), and so forth, have their customary meanings.

As used herein, the term "assay" and grammatical equivalents refers to tests, measurements, observations, and other experimental procedures which may be applied to a sample for detection of an analyte, identification of an analyte, and measurement of the amounts of an analyte in a sample. Assays may be physical assays which detect, identify, or measure a physical property of a sample; assays may be chemical assays, which detect, identify, or measure a chemical property of a sample, or perform chemical reactions in or with a sample; and include assays which use optical, electrical or electronic, chemical, or other means of detection and measurement.

As used herein, an "analyte" is the subject of an assay or analysis, the presence or amounts of which are to be determined by the performance of the assay. An analyte may be a natural constituent of a biological sample; an analyte may be free in a fluid sample or solution, or may be bound to another compound (e.g., to a carrier protein), may be present on a cell, or may be present in a cell; an analyte may be a compound not normally found in a biological sample, such as a drug; a metabolite of a drug or other compound; an infectious agent (e.g., a virus, bacteria, or other foreign organism or material); a toxin; or other compound, element, cell, or cellular marker that may be the subject of analysis. An analyte may comprise a cell, or virus, or portion thereof; and may comprise a physical or chemical characteristic of a cell, virus, tissue, or portion thereof.

An assay for an analyte is a test or procedure directed at detecting the presence of that analyte, or determining the amount of that analyte, or identifying that analyte, or characterizing that analyte, or otherwise obtaining information about that analyte, in a sample.

As used herein, the term "negative result" and grammatical equivalents thereof refers to a result of an assay in which the presence of the target analyte is not detected, or is detected at a normal level, in the biological sample.

As used herein, the term "positive result" and grammatical equivalents thereof refers to a result of an assay in which the presence of the target analyte is detected, or is detected at an abnormal level, in the biological sample.

As used herein, the terms "reflex test" and "reflex assay" refer to an assay (equivalently, a test) the performance of which is contingent on a result of a previous test (which may be termed an "initial test" or an "initial assay"). Whether or not the reflex test is performed, or the timing of, or order in which, the reflex test is performed, is determined by a result of the initial test.

As used herein, the term "contingent" refers to dependence on a prior event, result, condition, or state. Thus, where an act is contingent on a criterion (e.g., the occurrence of an act; the outcome of a test; the existence of a state or condition; or the satisfaction of a criterion of any kind) the performance of that act is conditional upon the criterion, and that act will occur or be performed, or not, or will occur or be performed in a particular way, depending upon that criterion. For example, one form of reflex test is one in which a positive result from a general test triggers an automatic test of a more specific nature; for example, an influenza reflex test which is positive for the presence of influenza virus may automatically trigger a more specific test which will identify the particular strain of influenza present in a sample from the subject, or will determine whether or not a particular strain of influenza is present in a sample from the subject.

As used herein, the term "contingent assay" refers to an assay the performance of which (or failure to perform) depends on a prior event or condition. For example, a contingent assay may be one that is performed only if the result of a prior assay satisfies a criterion (or criteria); a contingent assay may be one that is not performed if the result of a prior assay satisfies a criterion (or criteria); a contingent assay may be one that is performed in one way if the result of a prior assay satisfies a criterion (or criteria), but is performed in a different way if the criterion (or criteria) is (are) not met. Thus, a single contingent assay may depend upon a single criterion; or, a single contingent assay may depend upon multiple criteria. Multiple contingent assays may depend upon a single criterion; or, multiple contingent assays may depend upon multiple criteria.

Similarly, a step in an assay may be a "contingent step", i.e., one that is contingent upon the occurrence or outcome of a prior assay, or a prior step of an assay (including the assay in which a contingent step occurs).

As used herein, the term "antibody-based assay" refers to an assay for an analyte which may be found in a biological sample, using specific binding of the analyte by an antibody, antibody fragment, or antibody mimetic (e.g., immunoadhesin, aptamer, or other construct which specifically binds to a target with little or no cross-reactivity with other compounds) to detect the presence of, and, if desired, quantify the amounts of, an analyte in a sample. Thus, as used herein, the term "antibody-based assay" includes immunoassays (including ELISAs), receptor-based assays, and other assays which utilize specific binding between a receptor and a ligand to detect, identify, or quantify an analyte. A Western blot may be termed an antibody-based assay.

An aptamer is a nucleic acid molecule capable of binding to a target molecule. The nucleic acid may be a deoxyribonucleic acid, a ribonucleic acid, a linked peptide nucleic acid, or other nucleic acid, analog, or derivative thereof. The generation and use of aptamers is known in the art; see, e.g., U.S. Pat. No. 5,475,096.

The term "immunoadhesin" designates an antibody-like molecule which combines the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG4 subtypes, IgA (including IgA-1 and IgA-2), IgE, IgD or IgM Immunoadhesins reported in the literature include fusions of the T cell receptor (Gascoigne et al. Proc. Natl. Acad. Sci. USA 84:2936-2940 [1987]), CD4 (Capon et al., Nature 337:525-531 [1989]), CD44 (Aruffo et al., Cell 61:1303-1313 [1990]), and IgE receptor alpha (Ridgway et al., J. Cell. Biol. 115:abstr. 1448 [1991]). For the production of immunoglobulin fusions see also U.S. Pat. No. 5,428,130 issued Jun. 27, 1995.

As used herein, the term "cytometric assay" refers to an assay which detects, or identifies, or quantifies cells or particles in a sample, typically by optical means (e.g., by microscopy). For example, cells or particles may be counted in a sample, or a field of view within a sample, to provide a number, or density, or other numerical value regarding cells or particles in a sample. Size, or optical intensity, or other characteristic of cells or particles in a sample may be measured or characterized. Cells in a sample assayed in a cytometric assay may be labeled, or otherwise treated, to enhance their identification or to ease the differentiation between cells and cell types. Thus, for example, cell surface markers may be labeled and optically identified by exposure of cells to antibodies or antibody fragments directed at particular cell surface antigens, where the antibodies or antibody fragments are labeled with fluorescent dyes or other identifiable markers. In addition to antibodies and antibody fragments (and mimetics thereof), aptamers, immunoadhesins, nucleic acid molecules, nucleic acid mimetics, dyes, and other probes or labels specific for cellular features, organelles, molecules, or characteristics may also be used to identify and characterize cells in a cytometric assay.

As used herein, "measurement of a morphological characteristic" of a cell or particle, and grammatical variants thereof, refers to a cytometric assay directed at identifying, quantifying, or characterizing the size, shape, or other physical characteristic of a cell, particle, or group of cells or particles in a sample. Observation, measurement, or characterization of the appearance of a cell or particle is one type of measurement of a morphological characteristic. Measurement or characterization of the size of a cell or particle may refer to the measurement or characterization of the diameter, cross-sectional area, volume, or other characteristic of a cell or particle. Measurement or characterization of the shape of a cell or particle may refer to the measurement or characterization of the symmetry (or asymmetry), or presence or number of protrusions, smoothness (or roughness) of a cellular surface, or other characteristic of a cell or particle. Measurement or characterization of brightness, or other optical property, across a dimension of a cell or particle, comprises measurement of a morphological characteristic of a cell or particle. Other morphological characteristics may also be observed, measured and characterized.

The word "label" or "marker" or the phrases "detectable label" and "marker moiety" when used herein refer to a detectable compound or composition which is conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition which is detectable (a label may be, e.g., a dye, a fluorescent moiety, a luminescent moiety, a chemiluminescent moiety, an enzymatic label, a magnetic label, a paramagnetic label, a contrast agent, a nanoparticle, a radioisotope, an epitope tag, biotin, streptavidin, or a quencher). Dyes include, for example, fluorescent dyes that intercalculate with double-stranded DNA include, for example, SYBR Gold™, SYBR Green I™, SYBR Green II™, ethidium bromide, BlueView™, methylene blue, DAPI, and acridine orange. Further fluorescent dyes include, for example, CAL Fluor Gold, CAL Fluor Orange, Quasar 570, CAL Fluor Red 590, CAL Fluor Red 610, CAL Fluor Red 610, CAL Fluor Red 635, Quasar 670 (Biosearch Technologies), VIC, NED (Life Technologies), Cy3, Cy5, Cy5.5 (GE Healthcare Life Sciences), Oyster 556, Oyster 645 (Integrated DNA Technologies), LC red 610, LC red 610, LC red 640, LC red 670, LC red 705 (Roche Applies Science), Texas red, FAM, TET, HEX, JOE, TMR, and ROX. Quenchers that may be used include, for example, DDQ-I, DDQ-II (Eurogentec), Eclipse (Epoch Biosciences), Iowa Black FQ, Iowa Black RQ (Integrated DNA Technologies), BHQ-1, BHQ-2, BHQ-3 (Biosearch Technologies), QSY-7, QSY-21 (Molecular Probes), and Dabcyl.

As used herein, the term "small molecule" refers to a compound, typically a non-polymeric organic compound, that is smaller than a typical protein. Examples of small molecules include acetylsalicylic acid (aspirin), caffeine, cholesterol, vitamin D, and other molecules. A small molecule typically has a molecular weight below about 500 Daltons. As used herein, small molecules may be small organic molecules, and may be small inorganic molecules.

As used herein, the term "general chemistry assay" refers to an assay for an element or compound which may be found in a biological sample, using chemical or physical reactions to detect the presence of, and, if desired, quantify the amounts of, an analyte in a sample. As used herein, a "general chemistry assay" may be directed at detecting a small molecule analyte (including ions and elements such as sodium or potassium), or directed at a chemical characteristic of a sample (e.g., pH, $O_2$ saturation, or other sample characteristic determined by chemical means).

As used herein, the term "nucleic acid assay" refers to an assay for a nucleic acid (whether deoxyribonucleic acid (DNA) or ribonucleic acid (RNA)) which may be found in a biological sample; such assays typically use hybridization between a probe and the target nucleic acid to detect the presence of, and, if desired, quantify the amounts of, an analyte in a sample. Nucleic acid assays include, for example, polymerase chain reaction (PCR) assays of all types, Northern blots, Southern blots, and other assays.

"Stringency" of hybridization reactions is readily determinable by one of ordinary skill in the art, and generally is an empirical calculation dependent upon probe, length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/ 0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride. 75 mM sodium citrate at 42° C.; or (3) employ 50% formamide, 5×SSC (0.75 M NaCl, 0.075 M sodium citrate). 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C. with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% Formamide, 5×SSC (150 mM NaCl, 15 mM trisodium citrate). 50 mM sodium phosphate (pH 7.6). 5×Denhardt's solution. 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The terms "blood" and "whole blood" refer to blood as it exists within an animal and as directly obtained from a subject in a blood sample. Blood contains red blood cells, white blood cells, proteins such as albumin, globulins, and clotting factors, salts, water, and other constituents.

The terms "plasma" and "blood plasma" refer to the liquid portion of blood (e.g., a blood sample) that remains after the removal of blood cells. Red blood cells and white blood cells may be removed by centrifugation of a blood sample, leaving plasma above the pelleted cells in the bottom of the centrifuge tube. Plasma retains blood clotting factors, and is obtained from anti-coagulated blood samples.

The terms "serum" and "blood serum" refer to the liquid portion of blood that remains after blood is allowed to clot, and the clot is removed. Serum differs from plasma in that serum lacks clotting factors: since clotting requires fibrin, thrombin, and other proteins, which form and remain part of a blood clot, serum lacks these proteins while plasma contains them.

As used herein, a "finger-stick" refers to: i) the act of making a small puncture in the skin of a subject, allowing a small amount (e.g., a droplet, or one, two, or a few drops) of blood to flow and become available for collection; ii) the puncture itself; and iii) the blood collected thereby. Blood may be liberated in a finger-stick, for example, by use of a lancet or other sharp implement effective to pierce the skin of a subject. Typically, only a small amount of blood is collected in this way (e.g., the amount of blood may be about 250 µL or less, or about 200 µL or less, or about 150 µL or less, or about 100 µL or less, or about 50 µL or less, or about 25 µL or less, or about 15 µL or less, or about 10 µL or less, or about 10 µL or less, or about 5 µL or less, or about 3 µL or less, or about 1 µL or less). Blood from a finger-stick may be collected, e.g., by needle, syringe, capillary tube, or other method. Blood from a finger-stick may be collected for transport to another location; for storage prior to use or analysis; for immediate use; or for a combination of the same.

As used herein, the term "biological sample" refers to a fluid, tissue, or other material collected from a subject. Examples of biological samples can include but are not limited to, blood, serum, plasma, a throat swab, a nasal swab, a nasopharyngeal wash, saliva, urine, gastric fluid, cerebrospinal fluid, tears, stool, mucus, sweat, earwax, oil, a glandular secretion, semen, vaginal fluid, interstitial fluids derived from tumorous tissue, ocular fluids, breath, hair, finger nails, skin, biopsy tissue, placental fluid, amniotic fluid, cord blood, lymphatic fluids, cavity fluids, sputum, pus, microbiota, meconium, breast milk, and other secretions or excretions. Biological samples may include nasopharyngeal wash, or other fluid obtained by washing a body cavity or surface of a subject, or by washing a swab following application of the swab to a body cavity or surface of a subject. Nasal swabs, throat swabs, stool samples, hair, finger nail, ear wax, breath, and other solid, semi-solid, or gaseous samples may be processed in an extraction buffer, e.g., for a fixed or variable amount of time, prior to their analysis. The extraction buffer or an aliquot thereof may then be processed similarly to other fluid samples if desired. Examples of tissue samples of the subject may include but are not limited to, connective tissue, muscle tissue, nervous tissue, epithelial tissue, cartilage, cancerous sample, or bone. The sample may be obtained from a human or animal. The sample may be obtained from a mammal, vertebrate, such as murines, simians, humans, farm animals, sport animals, or pets. The sample may be obtained from a living or dead subject. The sample may be obtained fresh from a subject or may have undergone some form of pre-processing, storage, or transport.

As used herein, "portion" and "portions" (e.g., of biological samples) include, without limitation, aliquots (which may be of equal volume, or may be of unequal volume); dilutions (in which a sample, or a portion thereof, is mixed with a diluent to form a dilution of the sample); fractions (e.g., a fraction of whole blood, such as serum, or plasma, or a pellet formed by centrifugation); and combinations thereof.

Reflex Testing

Methods, devices, and systems disclosed herein may be used to provide and perform a "reflex test" in which a second assay is, or subsequent assays are, performed contingent on the results of an initial test or tests.

In embodiments, a reflex test may be performed upon obtaining negative results from an initial test. For example, a negative result may indicate that a subject does not suffer from a suspected disease or condition that was suggested by a particular symptom, and indicates that a different assay directed at a different suspected disease or condition should be performed. In such embodiments, a reflex test for the different suspected disease or condition may be performed, as a result of obtaining the negative results from the initial test.

In embodiments, a reflex test may be performed upon obtaining positive results from an initial test. For example, an initial test may be, e.g, an HIV test. In such an example, positive results of an antibody-based assay for HIV (e.g., an HIV-1 test, or an HIV-2 test) on a sample from a subject may trigger the testing of a sample from the same subject using a nucleic acid assay for HIV (e.g., a nucleic acid assay for HIV-1 test, or a nucleic acid assay for HIV-2 test). In embodiments, a positive result in an antibody-based HIV assay for HIV may trigger testing of a sample from the same subject in a nucleic acid assay. In embodiments, a positive result in an initial nucleic acid assay for HIV may trigger testing of a sample from the same subject by a subsequent, higher stringency nucleic acid assay for HIV. In embodiments, a positive result in an antibody-based HIV assay (e.g., an ELISA or other assay) may trigger testing of a sample from the same subject by Western blot (also an antibody-based assay) for HIV. In embodiments, a positive result in an antibody-based HIV assay may trigger testing of a sample from the same subject in a cytometric assay. In embodiments, a positive result in a nucleic acid assay for HIV may trigger testing of a sample from the same subject in a cytometric assay. In embodiments, a positive result in an antibody-based HIV assay for HIV may trigger testing of a sample from the same subject in a general chemistry assay. In embodiments, a positive result in a nucleic acid assay-based HIV assay for HIV may trigger testing of a sample from the same subject in a general chemistry assay. In embodiments, a positive result in a cytometric assay indicative of symptoms of HIV may trigger testing of a sample from the same subject in an antibody-based assay, or a nucleic acid assay, or in a general chemistry assay, or a combination of one or more of these assays. In embodiments, a positive result in any assay indicative of symptoms of HIV may trigger testing of a sample from the same subject in a cytometric assay, an antibody-based assay, or a nucleic acid assay, or in a general chemistry assay, or a combination of one or more of these assays.

It will be understood that the embodiments discussed above are exemplary, using HIV as an example, but that a biological sample may also be assayed and analysed analogously for any disease or condition by the methods, devices, and systems disclosed herein.

For a further example, an initial assay may comprise a complete blood cell count test, comprising testing a blood sample for white blood cells, where a white blood cell count outside the normal range (e.g., below about 2000 cells per microliter (μL) for males older than 12 years of age is outside the normal range) may trigger a reflex test comprising further testing of the blood of the subject. In embodiments, such further testing of the blood may be an automatic test performed by a cytometer on a device as disclosed herein. For example, such a reflex cytometric test may comprise identifying and/or quantifying white blood cells in the sample by cell type, using a cytometer. Such a cytometer test may be an automatic cytometer test, and may not require the intervention of any person to perform the cytometric assay. In embodiments, such further testing of the blood may be a "Manual" test performed by a trained person. In embodiments, such a reflex test comprising further testing of the blood may comprise both an automatic test performed by a cytometer on a device and a "Manual" test performed by a trained person.

For a further example, a positive test for hepatitis may trigger the further testing of a sample from the same subject. In embodiments, an initial test for hepatitis may comprise a test for analytes indicative of compromised liver function, e.g., increased serum aminotransferase levels, or increased alkaline phosphatase levels, or increased gamma-glutamyl transpeptidase levels, or increased bilirubin, or other blood marker which may be altered by hepatitis. In embodiments, such further testing of a sample from the subject may comprise an antibody-based assay. In embodiments, such further testing of a sample from the subject may comprise a nucleic acid assay. In embodiments, such further testing of a sample from the subject may comprise an automatic test performed by a cytometer on a device as disclosed herein.

For a further example, a positive test for hepatitis C may trigger the further testing of a sample from the same subject. In embodiments, an initial test for hepatitis C may comprise a test for the presence of antibodies to hepatitis C virus. In embodiments, such further testing of a sample from the subject may be a nucleic acid assay for the presence of nucleic acids indicative of hepatitis C virus. In embodiments, an initial test for hepatitis C may comprise an antibody-based assay for the presence of epitopes (antibody targets) indicative of the presence of hepatitis C virus in the sample. In embodiments, such further testing of a sample from the subject may be a nucleic acid assay for the presence of nucleic acids indicative of hepatitis C virus. In embodiments, an initial test for hepatitis C may comprise a test for the presence of nucleic acids indicative of hepatitis C virus. In embodiments, such further testing of a sample from the subject may be a nucleic acid assay for the presence of antibodies to hepatitis C virus.

For a further example, a positive test for the presence of syphilis may trigger the further testing of a sample from the same subject. In embodiments, an initial test for the presence of syphilis may comprise a nucleic acid test for the presence of nucleic acids indicative of syphilis bacteria. In embodiments, a subsequent test for the presence of syphilis may comprise a higher stringency nucleic acid test for the presence of syphilis bacteria (as compared to the stringency of the initial nucleic acid test for syphilis). In embodiments, a subsequent test for the presence of syphilis may comprise a Western blot test for the presence of syphilis bacteria.

In embodiments, an initial test for the presence of syphilis may comprise a test for the presence of antibodies to syphilis bacteria. In embodiments, such further testing of a sample from the subject may be an automatic test performed by a cytometer on a device as disclosed herein. In embodiments, an automatic test performed by a cytometer on a device as disclosed herein may be a cytometric test using darkfield illumination of a blood sample from the patient, in order to determine and/or quantify the presence of syphilis bacteria. In embodiments, such further testing may be a "Manual" test performed by a trained person.

An initial assay may comprise an assay for the presence of hepatitis B. For example, a sample obtained from a pregnant female may be tested for hepatitis B surface antigen (an antibody-based assay). If this initial test is found to be positive for the presence of hepatitis B surface antigen, a nucleic acid reflex test may be performed for a more sensitive and specific test for the hepatitis B virus; the reflex test may also provide quantification of the viral load in the sample. The nucleic acid reflex test may be performed on a different sample than the antibody-based hepatitis B surface antigen assay; this different sample may be a portion of the original sample, obtained by dividing the original sample into portions, and retained for future use if needed; this different sample may be a separate sample, obtained at the same, or nearly the same time, as the original sample, and retained for future use if needed; or this different sample may be a sample obtained after the original sample was obtained (e.g., after the result of the initial test was determined).

For a further example, a sample obtained from a pregnant female may be tested for hepatitis B surface antigen (an antibody-based assay). If this initial test is found to be positive for the presence of hepatitis B surface antigen, a reflex assay for the presence of syphilis may be performed. Such a reflex syphilis assay may be, for example, a nucleic acid reflex test for the presence of nucleic acids indicative of the presence of syphilis bacteria in the sample. In embodiments, such a reflex syphilis assay may be an antibody-based reflex test for the presence of proteins indicative of the presence of syphilis bacteria in the sample. In embodiments, such a reflex syphilis assay may be, for example, a cytometric assay for the presence of syphilis bacteria in the sample. The reflex test may be performed on a different sample than the antibody-based hepatitis B surface antigen assay; this different sample may be a portion of the original sample, obtained by dividing the original sample into portions, and retained for future use if needed; this different sample may be a separate sample, obtained at the same, or nearly the same time, as the original sample, and retained for future use if needed; or this different sample may be a sample obtained after the original sample was obtained (e.g., after the result of the initial test was determined).

For a further example, a urine sample may be assayed for the presence of blood, for the presence of nitrite, for the presence of more than trace amounts of protein, or for the presence of white blood cells (e.g., leukocytes) in the urine. In embodiments, an initial assay performed on a urine sample may be an antibody-based assay. If the results of such an antibody-based assay are found to be positive, then a reflex test may be performed, in which a sample of urine is subjected to cytometric testing. Such cytometric testing may be automated, or may be manual (i.e., involving observation of the sample by a technician using a microscope, or a camera, or both), or a combination of these. The cytometric reflex test may be performed on a different sample than the antibody-based initial assay; this different sample may be a portion of the original sample, obtained by dividing the original sample into portions, and retained for future use if needed; this different sample may be a separate sample, obtained at the same, or nearly the same time, as the original sample, and retained for future use if needed; or this different sample may be a sample obtained after the original sample was obtained (e.g., after the result of the initial test was determined).

For a further example, a urine sample may be assayed for the presence of blood, for the presence of nitrite, for the presence of more than trace amounts of protein, or for the presence of white blood cells (e.g., leukocytes) in the urine, as discussed above. In embodiments, an initial assay performed on a urine sample may be an antibody-based assay. If the results of such an antibody-based assay are found to be positive, then a reflex test may be performed, in which an assay for the presence of bacteria is performed, using a sample of urine. In embodiments, such an assay for the presence of bacteria in the urine comprises a bacterial culture, in which urine is applied to a substrate suitable for the culture of bacteria and the substrate incubated under conditions conducive to bacterial growth. Such a bacterial culture reflex test may be performed on a different sample than the antibody-based initial assay; this different sample may be a portion of the original sample, obtained by dividing the original sample into portions, and retained for future use if needed; this different sample may be a separate sample, obtained at the same, or nearly the same time, as the original sample, and retained for future use if needed; or this different sample may be a sample obtained after the original sample was obtained (e.g., after the result of the initial test was determined).

In embodiments, after providing a biological sample to a device, all assays are performed automatically by a device or system, e.g., by a device or system as disclosed herein. In embodiments, after providing a single biological sample to a device, all assays are performed automatically by a device or system, e.g., by a device or system as disclosed herein. In embodiments, after providing a plurality of biological samples to a device, all assays are performed automatically by a device or system, e.g., by a device or system as disclosed herein. In embodiments, after providing a biological sample to a device, an initial assay is performed automatically by a device or system, e.g., by a device or system as disclosed herein, and a further sample is requested; upon loading such further sample in a device, at least one subsequent assay is performed automatically on the subsequent sample by a device or system, e.g., by a device or system as disclosed herein. In embodiments, after providing a biological sample to a device, an initial assay is performed automatically by a device or system, e.g., by a device or system as disclosed herein, and a further sample is requested; upon loading such further sample in a device, all subsequent assays are performed automatically on the subsequent sample by a device or system, e.g., by a device or system as disclosed herein.

In embodiments, after providing a biological sample to a device, an initial assay is performed automatically by a device or system, e.g., by a device or system as disclosed herein, and a further sample is obtained automatically; at least one subsequent assay is performed on such subsequent sample automatically by a device or system, e.g., by a device or system as disclosed herein. In embodiments, after providing a biological sample to a device, an initial assay is performed automatically by a device or system, e.g., by a device or system as disclosed herein, and a further sample is obtained automatically; all subsequent assays are performed on such subsequent sample automatically by a device or system, e.g., by a device or system as disclosed herein.

Thus, in embodiments, reflex testing may be performed in response to an assay result. For example, the results of a first assay A may be determinative of whether or not a second assay B should be run; in this example, assay A is the initial assay, and assay B, contingent on the results of assay A, is the reflex assay. Thus, for example, when an assay A is ordered, a cartridge may be pre-loaded with reagents required by assay A, and also pre-loaded with reagents necessary for assay B. If the result of assay A meets a predefined criterion initiating the reflex assay, then assay B is run with the same sample in the device. The device protocol is planned to account for the possibility of running the reflex test (i.e., the necessary reagents are loaded into the cartridge, sufficient sample is obtained to perform both assay A and assay B, and sufficient sample is retained in reserve for running assay B if needed).

In embodiments, some protocol steps of assay B may be performed before the results for assay A are complete. For example, sample preparation can be completed in advance on the device.

In embodiments, a sample of sufficient size may be obtained from the subject sufficient to perform assay A and to perform assay B. In embodiments, a sample may be obtained from the subject, and may be diluted with a reagent (e.g., a diluent such as water, saline, a buffered solution, or other diluent) in order to provide sufficient volume of diluted sample to perform assay A and to perform assay B. In embodiments, a sample may be obtained from the subject, used to perform assay A, and stored in order to be available for the performance of assay B if indicated. In embodiments, a sample may be obtained from the subject, and divided into two portions, one of which may be used to perform assay A, and the other of which may be stored in order to be available for the performance of assay B if indicated. In embodiments, both portions of a sample divided into two portions (one of which may be used to perform assay A, and the other of which may be used to perform assay B) may be treated equivalently. In embodiments, the portions of a sample divided into two portions (one of which may be used to perform assay A, and the other of which may be used to perform assay B) may be treated differently from each other.

In embodiments, a reflex assay may be performed with a second sample from the patient. In such embodiments, a second sample may be obtained from the subject following the satisfaction of the criterion or criteria by the results of assay A. In embodiments, a result of assay A may trigger a request for a second, or a subsequent, sample. In embodiments, a request for a second, or a subsequent, sample may comprise a message, e.g., a message displayed on the device, a message displayed on an interface, a message sent to an electronic address (e.g., an email, or an internet posting, or a tweet, or other address of an electronic messaging system), a message to the subject, or to an operator of a device, or to a health-care provider, or to a payer (e.g., an insurance company), or more than one of these messages, or to more than one of these individuals or entities.

A second or subsequent sample may comprise same type of sample as the initial sample. A second or subsequent sample may comprise a different type of sample than the initial sample.

Alternatively, in such embodiments, a second sample may be obtained from the subject prior to the satisfaction of the criterion or criteria by the results of assay A; for example, two samples may be obtained from a subject at the same time, or may be obtained at different times prior to obtaining the results from the initial assay A. In embodiments, both samples may be treated equivalently. In embodiments, both samples may be treated differently from each other.

The assays and methods disclosed herein may be performed on a device, or on a system, for processing a sample. The assays and methods disclosed herein can be readily incorporated into and used in device for processing a sample, or a system for processing a sample, which may be an automated assay device, or may be an automated assay system. Such a device, and such a system, may be useful for the practice of the methods disclosed herein. For example, a device may be useful for receiving a sample. A device may be useful for preparing, or for processing a sample. A device may be useful for performing an assay on a sample. A device may be useful for obtaining data from a sample. A device may be useful for transmitting data obtained from a sample. A device may be useful for disposing of a sample following processing or assaying of a sample.

A device may be part of a system, a component of which may be a sample processing device. A device may be a sample processing device. A sample processing device may be configured to facilitate collection of a sample, prepare a sample for a clinical test, or effect a chemical reaction with one or more reagents or other chemical or physical processing, as disclosed herein. A sample processing device may be configured to obtain data from a sample. A sample processing device may be configured to transmit data obtained from a sample. A sample processing device may be configured to analyze data from a sample. A sample processing device may be configured to communicate with another device, or a laboratory, or an individual affiliated with a laboratory, to analyze data obtained from a sample.

A sample processing device may be configured to accept a sample from a subject, either directly or indirectly. A sample may be, for example, a blood sample (e.g., a sample obtained from a fingerstick, or from venipuncture, or an arterial blood sample), a urine sample, a biopsy sample, a tissue slice, stool sample, or other biological sample; a water sample, a soil sample, a food sample, an air sample; or other sample. A blood sample may comprise, e.g., whole blood, plasma, or serum. A sample processing device may receive a sample from the subject through a housing of the device. The sample collection may occur at a sample collection site, or elsewhere. The sample may be provided to the device at a sample collection site.

Examples of samples may include various fluid or solid samples. In some instances, the sample can be a bodily fluid sample from the subject. The sample can be an aqueous or gaseous sample. In some instances, solid or semi-solid samples can be provided. The sample can include tissues and/or cells collected from the subject. The sample can be a biological sample.

Any volume of sample may be obtained from a subject. Examples of volumes may include, but are not limited to, about 10 mL or less, 5 mL or less, 3 mL or less, 1 microliter (μL, also "uL" herein) or less, 500 μL or less, 300 μL or less, 250 μL or less, 200 μL or less, 170 μL or less, 150 μL or less, 125 μL or less, 100 μL or less, 75 μL or less, 50 μL or less, 25 μL or less, 20 μL or less, 15 μL or less, 10 μL or less, 5 μL or less, 3 μL or less, 1 μL or less, 500 μL or less, 250 μL or less, 100 μL or less, 50 μL or less, 20 μL or less, 10 μL or less, 5 μL or less, 1 μL or less, 500 pL or less, 100 pL or less, 50 pL or less, or 1 pL or less. In embodiments, a biological sample may have a volume of 250 μL or less. In embodiments, a biological sample may have a volume of 100 μL or less. In embodiments, a biological sample may have a volume of 50 μL or less. The amount of sample may be about a drop of a sample. The amount of sample may be the amount collected from a pricked finger or fingerstick. The amount of sample may be the amount collected from a microneedle or a venous draw. Any volume, including those described herein, may be provided to the device.

In embodiments, a biological sample may include cells.

In some embodiments, a sample processing device may be configured to accept or hold a cartridge. In some embodiments, a sample processing device may comprise a cartridge. The cartridge may be removable from the sample processing device. In some embodiments, a sample may be provided to the cartridge of the sample processing device. Alternatively, a sample may be provided to another portion of a sample processing device. The cartridge and/or device may comprise a sample collection unit that may be configured to accept a sample.

A cartridge may include a sample, and may include reagents for use in processing or testing a sample, disposables for use in processing or testing a sample, or other materials. Following placement of a cartridge on, or insertion of a cartridge into, a sample processing device, one or more components of the cartridge may be brought into fluid communication with other components of the sample processing device. For example, if a sample is collected at a cartridge, the sample may be transferred to other portions of the sample processing device. Similarly, if one or more reagents are provided on a cartridge, the reagents may be transferred to other portions of the sample processing device, or other components of the sample processing device may be brought to the reagents. In some embodiments, the reagents or components of a cartridge may remain on-board the cartridge. In some embodiments, no fluidics are included that require tubing or that require maintenance (e.g., manual or automated maintenance).

In embodiments, a cartridge may include a biological sample, or may include two or more biological samples. In embodiments, a biological sample is from a subject, and multiple biological samples may be from a single subject. In alternative embodiments, multiple biological samples may be from multiple subjects. A cartridge that has one or more identifier that is readable by the device. The device may include an automated lancing cartridge. The cartridge may be disposable. One or more disposable component may be used to collect a sample from a subject. The disposable component may provide the sample to a non-disposable device. Alternatively, the disposable component may be the sample processing device.

In embodiments, a cartridge may include a reagent or a plurality of reagents, and may be configured to allow delivery of said reagent or reagents to said device. A cartridge may be configured to deliver a biological sample and a reagent to the device. A cartridge may be configured to deliver a plurality of biological samples and a reagent to the device. A cartridge may be configured to deliver a biological sample and a plurality of reagents to the device. A cartridge may be configured to deliver a plurality of biological samples and a plurality of reagents to the device. Identification information may include subject identifying information, information based on signals generated related to the sample, information based on signals generated related to reactions performed with the sample, information based on signals detected related to the sample, information based on signals detected related to reactions performed with the sample, device identification information, cartridge identification information, component identifying information, and other information transmitted from the device.

A sample or reagent carried by a cartridge may be transferred to a device, such as a sample processing device. A sample or reagent may be transferred within a device. Such transfer of sample or reagent may be accomplished without providing a continuous fluid pathway from cartridge to device. Such transfer of sample or reagent may be accomplished without providing a continuous fluid pathway within a device. In embodiments, such transfer of sample or reagent may be accomplished by a fluid handling system (e.g., a pipette); for example, a sample, reagent, or aliquot thereof may be aspirated into an open-tipped transfer component, such as a pipette tip, which may be operably connected to a fluid handling system which transfers the tip, with the sample, reagent, or aliquot thereof contained within the tip, to a location on or within the sample processing device. The sample, reagent, or aliquot thereof can be deposited at a location on or within the sample processing device. Sample and reagent, or multiple reagents, may be mixed using a fluid handling system in a similar manner. One or more components of the cartridge may be transferred in an automated fashion to other portions of the sample processing device, and vice versa.

In embodiments of the devices, systems and methods disclosed herein, a fluid handling system may be used to transport and deliver a sample solution to a vessel, and to fill a vessel (either partially or fully) with a sample solution. In embodiments, a fluid handling system comprises a pipette. A pipette may be configured to accept a pipette tip, e.g., to mount and transport a pipette tip attached to the pipette. In embodiments, a pipette comprises a nozzle configured to accept a pipette tip. A pipette may be configured to aspirate a fluid, such as a sample solution, into a pipette tip attached to the pipette (e.g., a pipette tip which is attached to a nozzle of the pipette). In embodiments, a pipette may be configured to dispense a fluid, such as a sample solution, from a pipette tip attached to the pipette (e.g., to a nozzle of the pipette). A pipette may be configured to transmit force to a surface or component of a device. In embodiments, a pipette nozzle may contact a surface or component of a device, effective to transmit force to that surface or component. In embodiments, a pipette nozzle may contact a mating recess of a vessel, and, in embodiments, may engage a mating recess of a vessel. In embodiments, two, or more pipette nozzles may contact mating recesses of a vessel, and, in embodiments, may engage mating recesses of a vessel. In embodiments, a pipette of a fluid handling system may be movable, and is preferably movable in at least two, and more preferably in three dimensions (e.g., is movable in one, two, or all three of horizontally, laterally, and vertically).

A device, such as a sample processing device, may have a fluid handling system. A fluid handling system may perform, or may aid in performing, transport, dilution, extraction, aliquotting, mixing, and other actions with a fluid, such as a sample. In some embodiments, a fluid handling system may be contained within a device housing. A fluid handling system may permit the collection, delivery, processing and/or transport of a fluid, dissolution of dry reagents, mixing of liquid and/or dry reagents with a liquid, as well as collection, delivery, processing and/or transport of non-fluidic components, samples, or materials. The fluid may be a sample, a reagent, diluent, wash, dye, or any other fluid that may be used by the device, and may include, but not limited to, homogenous fluids, different liquids, emulsions, suspensions, and other fluids. A fluid handling system, including without limitation a pipette, may also be used to transport vessels (with or without fluid contained therein) around the device. The fluid handling system may dispense or aspirate a fluid. The sample may include one or more particulate or solid matter floating within a fluid.

In embodiments, a fluid handling system may comprise a pipette, pipette tip, syringe, capillary, or other component. The fluid handling system may have portion with an interior surface and an exterior surface and an open end. The fluid handling system may comprise a pipette, which may include a pipette body and a pipette nozzle, and may comprise a pipette tip. A pipette tip may or may not be removable from a pipette nozzle. In embodiments, a fluid handling system may use a pipette mated with a pipette tip; a pipette tip may be disposable. A tip may form a fluid-tight seal when mated with a pipette. A pipette tip may be used once, twice, or more times. In embodiments, a fluid handling system may use a pipette or similar device, with or without a pipette tip, to aspirate, dispense, mix, transport, or otherwise handle the fluid. The fluid may be dispensed from the fluid handling system when desired. The fluid may be contained within a pipette tip prior to being dispensed, e.g., from an orifice in the pipette tip. In embodiments, or instances during use, all of the fluid may be dispensed; in other embodiments, or instances during use, a portion of the fluid within a tip may be dispensed. A pipette may selectively aspirate a fluid. The pipette may aspirate a selected amount of fluid. The pipette may be capable of actuating stirring mechanisms to mix the fluid within the tip or within a vessel. The pipette may incorporate tips or vessels creating continuous flow loops for mixing, including of materials or reagents that are in non-liquid form. A pipette tip may also facilitate mixture by metered delivery of multiple fluids simultaneously or in sequence, such as in two-part substrate reactions.

The fluid handling system may include one or more fluidically isolated or hydraulically independent units. For example, the fluid handling system may include one, two, or more pipette tips. The pipette tips may be configured to accept and confine a fluid. The tips may be fluidically isolated from or hydraulically independent of one another. The fluid contained within each tip may be fluidically isolated or hydraulically independent from one fluids in other tips and from other fluids within the device. The fluidically isolated or hydraulically independent units may be movable relative to other portions of the device and/or one another. The fluidically isolated or hydraulically independent units may be individually movable. A fluid handling system may comprise one or more base or support. A base or support may support one or more pipette or pipette units. A base or support may connect one or more pipettes of the fluid handling system to one another.

A sample processing device may be configured to perform processing steps or actions on a sample obtained from a subject. Sample processing may include sample preparation, including, e.g., sample dilution, division of a sample into aliquots, extraction, contact with a reagent, filtration, separation, centrifugation, or other preparatory or processing action or step. A sample processing device may be configured to perform one or more sample preparation action or step on the sample. Optionally, a sample may be prepared for a chemical reaction and/or physical processing step. A sample preparation action or step may include one or more of the following: centrifugation, separation, filtration, dilution, enriching, purification, precipitation, incubation, pipetting, transport, chromatography, cell lysis, cytometry, pulverization, grinding, activation, ultrasonication, micro column processing, processing with magnetic beads, processing with nanoparticles, or other sample preparation action or steps. For example, sample preparation may include one or more step to separate blood into serum and/or particulate fractions, or to separate any other sample into various components. Sample preparation may include one or more step to dilute and/or concentrate a sample, such as a blood sample, or other biological samples. Sample preparation may include adding an anti-coagulant or other ingredients to a sample. Sample preparation may also include purification of a sample. In embodiments, all sample processing, preparation, or assay actions or steps are performed by a single device. In embodiments, all sample processing, preparation, or assay actions or steps are performed within a housing of a single device. In embodiments, most sample processing, preparation, or assay actions or steps are performed by a single device, and may be performed within a housing of a single device. In embodiments, many sample processing, preparation, or assay actions or steps are performed by a single device, and may be performed within a housing of a single device. In embodiments, sample processing, preparation, or assay actions or steps may be performed by more than one device.

A sample processing device may be configured to run one or more assay on a sample, and to obtain data from the sample. An assay may include one or more physical or chemical treatments, and may include running one or more chemical or physical reactions. A sample processing device may be configured to perform one, two or more assays on a small sample of bodily fluid. One or more chemical reaction may take place on a sample having a volume, as described elsewhere herein. For example one or more chemical reaction may take place in a pill having less than femtoliter volumes. In an instance, the sample collection unit is configured to receive a volume of the bodily fluid sample equivalent to a single drop or less of sample or interstitial fluid. In embodiments, the volume of a sample may be a small volume, where a small volume may be a volume that is less than about 1000 µL, or less than about 500 µL, or less than about 250 µL, or less than about 150 µL, or less than about 100 µL, or less than about 75 µL, or less than about 50 µL, or less than about 40 µL, or less than about 20 µL, or less than about 10 µL, or other small volume. In embodiments, all sample assay actions or steps are performed by a single device. In embodiments, sample processing, preparation, or assay actions or steps may be performed by more than one device.

A sample processing device may be configured to perform a plurality of assays on a sample. In embodiments, a sample processing device may be configured to perform a plurality of assays on a single sample. A plurality of assays may be run simultaneously; may be run sequentially; or some assays may be run simultaneously while others are run sequentially. One or more control assays and/or calibrators (e.g., including a configuration with a control of a calibrator for the assay/tests) can also be incorporated into the device; control assays and assay on calibrators may be performed simultaneously with assays performed on a sample, or may be performed before or after assays performed on a sample, or any combination thereof. In embodiments, many sample assay actions or steps, of a plurality of assays, are performed by a single device, and may be performed within a housing of a single device. In embodiments, sample processing, preparation, or assay actions or steps may be performed by more than one device.

In embodiments, devices, and systems and methods comprising or using such devices, may comprise a detector configured to detect analyte in a sample. A detector may be, for example, an optical detector, such as a spectrophotometer, a photomultiplier, a charge-coupled device, a camera, or other device or system configured to detect a light-based signal indicative of the presence of a analyte. In embodiments, a detector may be configured to, or be effective to, detect a signal comprising chemiluminescence, luminescence, fluorescence, absorbance, transmittance, turbidity, a color change, or other change in light, whether emitted, transmitted, or absorbed, effective to signal the presence of a analyte in a sample. In embodiments, a detector may comprise an electrochemical detector, or a temperature sensor, or a pH sensor, or a radiation sensor, or an ion-sensitive electrode, or other sensor capable of detecting the presence of a analyte in a sample.

Methods for detecting analyte include assays for detecting nucleic acids (e.g., DNA or RNA), assays for detecting peptides and proteins (including glycoproteins), assays for detecting other pathogen-related molecules, complement fixation assays, hemagglutination assays (e.g., for influenza), and other assays. Methods for detecting nucleic acids may be termed "nucleic acid assays" and include polymerase chain reaction (PCR) methods (including quantitative PCR (qPCR), reverse-transcriptase PCD (RT-PCR), "real-time" PCR, one-step PCR, two-step PCR, and other methods known in the art. Methods for detecting peptides and proteins include "antibody-based assays" such as, e.g., enzyme immunoassays such as Enzyme-Linked Immu-noSorbent Assays (ELISAs) and other assays utilizing antibodies or antibody fragments, complement-based reactions, measurement of absorbance of ultraviolet or other frequency of light, assays utilizing specific receptor-ligand interactions, and other assays known in the art. Assays for detecting other pathogen-related molecules include assays for bacterial sugars and lipids (e.g., bacterial lipopolysaccharide (LPS)), and other assays known in the art. A detector for use with such assays may be an optical detector, a pH detector, an electrochemical detector, a temperature sensor, an ion-sensitive electrode, a radiation detector, or other detector.

A sample processing device may be configured to detect one or more signals relating to the sample. A sample processing device may be configured to identify one or more properties of the sample. For instance, the sample processing device may be configured to detect the presence or concentration of one analyte or a plurality of analytes or a disease condition in the sample (e.g., in or through a bodily fluid, secretion, tissue, or other sample). Alternatively, the sample processing device may be configured to detect a signal or signals that may be analyzed to detect the presence or concentration of one or more analytes (which may be indicative of a disease condition) or a disease condition in the sample. The signals may be analyzed on board the device, or at another location. Running a clinical test may or may not include any analysis or comparison of data collected.

A chemical reaction or other processing step may be performed, with or without the sample. Examples of steps, tests, or assays that may be prepared or run by the device may include, but are not limited to immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidmetric assay, agglutination assay, radioisotope assay, viscometric assay, coagulation assay, clotting time assay, protein synthesis assay, histological assay, culture assay, osmolarity assay, and/or other types of assays, centrifugation, separation, filtration, dilution, enriching, purification, precipitation, pulverization, incubation, pipetting, transport, cell lysis, or other sample preparation action or steps, or combinations thereof. Steps, tests, or assays that may be prepared or run by the device may include imaging, including microscopy, cytometry, and other techniques preparing or utilizing images. Steps, tests, or assays that may be prepared or run by the device may further include an assessment of histology, morphology, kinematics, dynamics, and/or state of a sample, which may include such assessment for cells.

A device may be capable of performing all on-board steps (e.g., steps or actions performed by a single device) prior to the performance of a reflex test in a short amount of time. A device may be capable of performing all on-board steps on a single sample in a short amount of time prior to the performance of a reflex test. For example, from sample collection from a subject to transmitting data and/or to analysis prior to the performance of a reflex test may take about 3 hours or less, about 2 hours or less, about 1 hour or less, about 50 minutes or less, about 45 minutes or less, about 40 minutes or less, about 30 minutes or less, about 20 minutes or less, about 15 minutes or less, about 10 minutes or less, about 5 minutes or less, about 4 minutes or less, about 3 minutes or less, about 2 minutes or less, or about 1 minute or less. The amount of time from accepting a sample within the device to transmitting data and/or to analysis from the device regarding such a sample may depend on the type or number of steps, tests, or assays performed on the sample.

The amount of time from accepting a sample within the device to transmitting data and/or to analysis from the device regarding such a sample, prior to the performance of a reflex test, may take about 3 hours or less, about 2 hours or less, about 1 hour or less, about 50 minutes or less, about 45 minutes or less, about 40 minutes or less, about 30 minutes or less, about 20 minutes or less, about 15 minutes or less, about 10 minutes or less, about 5 minutes or less, about 4 minutes or less, about 3 minutes or less, about 2 minutes or less, or about 1 minute or less.

A device may be configured to prepare a sample for disposal, or to dispose of a sample, such as a biological sample, following processing or assaying of a sample.

In embodiments, a sample processing device may be configured to transmit data obtained from a sample. In embodiments, a sample processing device may be configured to communicate over a network. A sample processing device may include a communication module that may interface with the network. A sample processing device may be connected to the network via a wired connection or wirelessly. The network may be a local area network (LAN) or a wide area network (WAN) such as the Internet. In some embodiments, the network may be a personal area network. The network may include the cloud. The sample processing device may be connected to the network without requiring an intermediary device, or an intermediary device may be required to connect a sample processing device to a network. A sample processing device may communicate over a network with another device, which may be any type of networked device, including but not limited to a personal computer, server computer, or laptop computer; personal digital assistants (PDAs) such as a Windows CE device; phones such as cellular phones, smartphones (e.g., iPhone, Android, Blackberry, etc.), or location-aware portable phones (such as GPS); a roaming device, such as a network-connected roaming device; a wireless device such as a wireless email device or other device capable of communicating wireless with a computer network; or any other type of network device that may communicate possibly over a network and handle electronic transactions. Such communication may include providing data to a cloud computing infrastructure or any other type of data storage infrastructure which may be accessed by other devices.

A sample processing device may provide data regarding a sample to, e.g., a health care professional, a health care professional location, such as a laboratory, or an affiliate thereof. One or more of a laboratory, health care professional, or subject may have a network device able to receive or access data provided by the sample processing device. A sample processing device may be configured to provide data regarding a sample to a database. A sample processing device may be configured to provide data regarding a sample to an electronic medical records system, to a laboratory information system, to a laboratory automation system, or other system or software. A sample processing device may provide data in the form of a report.

In embodiments, devices, and systems and methods comprising or using such devices, may comprise a controller. In embodiments, a controller may comprise a processor. In embodiments, a controller may be connected to, and may control the operation of, components of a device; such components are typically disposed within a housing of the device. In embodiments, a controller may control the operation of a fluid handling system. In embodiments, a controller may control the operation of a detector. In embodiments, a controller may control the operation of any component or unit of the device. Other components may include, for example, a camera, a chemistry assay unit, a nucleic acid assay unit, a heating unit, a communication unit, a protein chemistry unit, or other component or unit. In embodiments, a controller may control the operation of one or more components of a device according to a protocol. In embodiments, a protocol by which a controller controls the operation of any one or more component or unit of a device may be preprogrammed, e.g., may be resident on the device. In embodiments, a protocol by which a controller controls the operation of any one or more component or unit of a device may be obtained from another device, or from a user, or from a laboratory, or from a network, or from the cloud. In embodiments, a protocol by which a controller controls the operation of any one or more component or unit of a device may be updated, or may be updatable, according to information or instructions from another device, or from a user, or from a laboratory, or from a network, or from the cloud. In embodiments, a device may receive information, or instructions, or updates, or protocols, via a user interface. In embodiments, a device may receive information, or instructions, or updates, or protocols, via a communication assembly.

In embodiments, devices, and systems and methods comprising or using such devices, may comprise a display effective to provide a user with information regarding the operation of the device, information regarding the progress of an assay performed by the device, or information regarding the results of an assay performed by the device. In embodiments, a display may comprise a visual display, or may comprise a printed display, or may comprise an audio signal, which may include an audio signal understandable as speech by a user, or may comprise any combination or all of such displays. In embodiments, a display may comprise a user interface. In embodiments in which a display comprises a user interface, a device may receive, e.g., information, commands, protocols, or other input. For example, a user interface may communicate a request for a second, or subsequent, biological sample. For example, a user interface may communicate instructions regarding obtaining a second, or subsequent, biological sample.

In embodiments, devices, and systems and methods comprising or using such devices, may comprise a communication assembly effective to communicate with one or more of a user, another device, a laboratory, a network, the cloud, or other communication target. In embodiments, a communication assembly may provide a communication target with information regarding the operation of the device, information regarding the progress of an assay performed by the device, or information regarding the results of an assay performed by the device. In embodiments, a communication assembly may be configured to allow a device to receive, e.g., information, commands, protocols, or other input from an outside source, such as, e.g., a user, another device, a laboratory, a network, the cloud, or other communication source.

In embodiments, a protocol may include instructions regarding one or more of: preparation of a sample; preparation of a plurality of samples; performing a chemical reaction; performing a plurality of chemical reactions; sequence of performing a plurality of chemical reactions; performing a clinical test; performing a plurality of clinical tests; sequence of performing a plurality of clinical tests; detecting the presence of an analyte; detecting the presences of a plurality of analytes; sequence of detecting the presences of a plurality of analytes; detecting the concentration of an analyte; detecting the concentrations of a plurality of analytes; sequence of detecting the concentrations of a plurality of analytes; pre-processing data; and sequence of steps in processing data. In embodiments, protocol information may be changed according to transmitted data obtained from said biological sample within said housing of said device according to said protocol.

Embodiments of the methods and assays disclosed herein are further described in the following examples.

Example 1

HIV Assays

Assays for the detection of human immunodeficiency virus (HIV) in a biological sample typically report negative results, i.e., no HIV is detected in the sample. However, since detection of the virus in a biological sample is of such importance, and may have such dire consequences for the subject from whom the sample was obtained, Applicant discloses methods for performing confirmatory follow-up testing on the basis of positive results to an initial assay. In embodiments, such confirmatory follow-up testing may be performed prior to reporting positive assay results to a health-care provider or to a subject. In embodiments, such confirmatory follow-up testing may be performed concurrent with, or following, the reporting of positive assay results to a health-care provider or to a subject.

In embodiments, an anti-HIV antibody screening test may be performed on a biological sample obtained from a subject; for example, an anti-HIV antibody screening test may be performed on a sample of blood obtained from a subject. In embodiments, an anti-HIV antibody screening test may be performed on a sample of a bodily fluid obtained from a subject other than a blood sample; such a sample may be, for example, a sample of urine, sputum, semen, tears, interstitial fluid, a sample obtained from a nasal swab, a sample obtained from a throat swab, a sample obtained from a vaginal swab, or other sample. In embodiments, a sufficient amount of a biological sample is obtained so as to allow the automatic reflex testing of the sample, or of a portion of the sample, without need to obtain a further sample in order to perform a further assay. In embodiments, only the amount of a biological sample needed for an initial assay or assays is obtained; in such an embodiment, a further biological sample must later be obtained if needed in order to perform a further assay contingent on the results of an initial assay.

For example, an antibody-based assay may comprise contacting a sample with a substrate to which antibodies specific for a target antigen are bound. In embodiments of such an antibody-based assay, the sample may be mixed, or diluted, with a reagent containing a known amount of labeled conjugate, where the labeled conjugate binds the bound antibodies. For example, the labeled conjugate may be a conjugate comprising the target analyte covalently linked with a detectable label. The mixture of sample and reagent may be then added to a chamber containing the substrate to which the antibodies are bound, and left to incubate for a sufficient time for target analyte, and analyte-conjugate, to bind to the substrate. Following the incubation period, the chamber may be washed with a washing solution, in order to wash out any remaining unbound analyte and unbound analyte-conjugate. After washing, the amount of labeled conjugate bound to the substrate may be determined, and the amount of target analyte in the sample determined. Such a determination may be made, e.g., by comparison with the amount of labeled conjugate bound in the absence of any target, and optionally by comparison with the amount of labeled conjugate bound in the presence of one or more known amounts of, or otherwise by comparison with control values, such as with a control curve. For example, after washing, a reagent allowing the detection of the label may be added to the chamber (e.g., where the label is an chemiluminescent label which emits light in the presence of a substrate, the reagent allowing the detection of the label may comprise the required substrate).

In embodiments, the anti-HIV antibody screening test may comprise an anti-HIV-1 antibody screening test. In embodiments, the anti-HIV antibody screening test may comprise an anti-HIV-2 antibody screening test. In embodiments, the anti-HIV antibody screening test may comprise an anti-HIV-1 and an anti-HIV-2 antibody screening test. In embodiments, the possible results of such an assay may comprise a result reporting that the sample is negative for the presence of HIV-1, and may comprise a result reporting that the sample is positive for the presence of HIV-1; in such embodiments, a normal result comprises a result reporting that the sample is negative for the presence of HIV-1. In embodiments, the possible results of such an assay may comprise a result reporting that the sample is negative for the presence of HIV-2, and may comprise a result reporting that the sample is positive for the presence of HIV-2; in such embodiments, a normal result comprises a result reporting that the sample is negative for the presence of HIV-2.

As disclosed herein, where the result of such a test comprises a result that the sample is negative for the presence of HIV-1, or negative for the presence of HIV-2, no further HIV test is automatically performed. As disclosed herein, where the HIV test comprises testing for the presence of both HIV-1 and HIV-2, and the result of such a test comprises a result that the sample is negative for the presence of HIV-1 and is negative for the presence of HIV-2, no further HIV test is automatically performed.

As disclosed herein, where the result of such a test comprises a result that the sample is positive for the presence of HIV-1, or is positive for the presence of HIV-2, or is positive for the presence of both HIV-1 and HIV-2, a further HIV test is automatically performed. Such a further HIV test may be performed on the same sample, or on an additional sample. In embodiments where the further HIV test is performed on an additional sample, the additional sample may be, or may be obtained from, a sample that was originally obtained from the subject; or, in embodiments, a further sample may be obtained from the subject and used for the further HIV test.

In embodiments, where a further HIV test is automatically performed subsequent to a positive result obtained from an initial HIV test, the further HIV test may comprise a nucleic acid assay. For example, in embodiments, where a further HIV test is automatically performed subsequent to a positive result obtained from an initial HIV test, the further HIV test may comprise a Western Blot HIV test.

In embodiments, the possible results of such a further HIV test may comprise a result reporting that the sample is negative for the presence of HIV-1, or is negative for the presence of HIV-2, or is negative for the presence of both HIV-1 and HIV-2. In such embodiments, a normal result comprises a result reporting that the sample is negative for the presence of HIV. As disclosed herein, where the result of a further HIV test comprises a result that the sample is negative for the presence of HIV-1, or negative for the presence of HIV-2, no further HIV test is automatically performed. Such results may be reported to a health-care provider, or to a subject, if appropriate, as indicating that the biological sample obtained from the subject is free of HIV.

However, in embodiments, results of such a further HIV test may comprise a result reporting that the sample is positive for the presence of HIV-1, or is positive for the presence of HIV-2, or is positive for the presence of both HIV-1 and HIV-2.

However, where the result of a further HIV test comprises a result that the sample is positive for the presence of HIV-1, or positive for the presence of HIV-2, such a result indicates that HIV was present in the biological sample obtained from the subject. Accordingly, such results indicate that the subject may suffer from HIV. Such results may be reported to a health-care provider, or to a subject, if appropriate, as indicating that the biological sample obtained from the subject contains HIV.

Additional testing may be indicated in the event of a positive result for either HIV-1 or HIV-2. For example, since HIV is a disorder of the immune system, cytometric testing directed to blood, and particularly to white blood cells, in which the blood cells in a sample of blood obtained from a patient, may be performed contingent on positive HIV results. Examples of cytometric tests are provided herein in a subsequent example.

Example 2

White Blood Cell Count Assays

In embodiments, an initial assay may be an assay for the determination of the white blood cell count of a sample of blood obtained from a subject. For example, white blood cell count may be obtained as part of a complete blood cell count. A white blood cell count assay may determine that the white blood cell count of blood obtained from a subject falls outside a normal range, e.g., may be below about 2000 cells per microliter ($\mu$L). Where an initial white blood cell count assay result determines that the white blood cell count of a blood sample is outside of a normal range, a reflex blood test may be required. Accordingly, Applicant discloses methods for performing confirmatory follow-up testing on the basis of white blood cell count results that fall outside of a pre-determined range. In embodiments, such confirmatory follow-up testing may be performed prior to reporting the initial white blood cell count results to a health-care provider or to a subject.

For example a normal range for an adult male subject (e.g., a male subject over the age of 12) may be between 3200 white blood cells/$\mu$L and 10,600 white blood cells/$\mu$L. If the result of an initial test is that a blood sample has a white blood cell count of less than 2000 white blood cells/$\mu$L (e.g., a white blood cell count of 1800 cells/$\mu$L), then a reflex blood test may be performed. Such a reflex blood test may comprise cytometric examination of the blood of the subject, such as a cytometric examination of white blood cells in a sample of blood from the subject. In embodiments, the sample of blood examined in the reflex assay may be a portion of the sample of blood that was examined in the initial test, e.g., where a portion of the sample was retained for further testing. In embodiments, the sample of blood examined in the reflex assay may be a sample of blood that was obtained at the same time as the sample of blood that was examined in the initial test, e.g., where a second blood sample was obtained and retained for further testing. In embodiments, a subsequent sample of blood may be obtained from the subject for reflex testing at a time after the time at which the initial sample of blood was obtained. In embodiments, the subsequent sample of blood may be obtained following determination of the results of the initial assay.

As discussed in more detail in the following Example, an automatic cytometric assay may be used to identify, quantify, and classify white blood cells in a sample. Blood samples may be pre-treated so as to avoid interference by red blood cells and platelets, e.g., by causing swelling and lysis of red blood cells and platelets, allowing white blood cells to settle and attach to a substrate, or by other means. White blood cells may be contacted with one or more labels specific for cell markers, which are thus useful for identifying and classifying the white blood cells. Such labels may include labels, such as fluorescent labels, to ease the detection of the labels and of cells labeled thereby.

Example 3

Cytometry

Assays and tests that may be contingent on the results of an initial test may include assays and tests that observe and describe cells in a biological sample, including assays and tests that identify cells, that determine the numbers of cells of one or more populations of cells, or that determine whether or not abnormal cells are present, or whether or not abnormal numbers of a cell type or cell types are present. Such tests and assays may utilize cytometry.

Cytometry may include preparing and analyzing two-dimensional images of cells in a biological sample, where the cells are labeled (e.g., with fluorescent, chemiluminescent, enzymatic, or other labels) and plated (e.g., allowed to settle on a substrate) and imaged by a camera. The camera may include a lens, and may be attached to or used in conjunction with a microscope. Cells may be identified in the two-dimensional images by their attached labels (e.g., from light emitted by the labels).

80 microliters of whole blood obtained from a fingerstick was loaded into a capped vessel preloaded with 2 mg/ml EDTA. The capped vessel was centrifuged at 1200×g for 5 minutes, to separate the blood cells from the blood plasma. Centrifugation of the capped vessel resulted in the separation of the blood sample in the capped vessel into two major components (from top of the capped vessel to the bottom): 1) blood plasma and 2) packed blood cells. This process ensures that no droplets of blood remain isolated, but coalesce with the main body of the liquid. In addition, this process separates the cells from elements of the plasma thus reducing metabolism and allowing for longer storage of the sample.

The centrifuged capped vessel was loaded into a cartridge containing multiple fluidically isolated reagents, tips, and a cytometry cuvette. The cartridge contained all the reagents required for the assay. The cartridge was loaded into a device equipped with at least a centrifuge, a pipette and a platform to load the cuvette. The pipette in the device has a plurality of nozzles, some nozzles being of a different size than some other nozzles.

Inside the device, a nozzle on the pipette was lowered on a cuvette carrier tool causing it to engage a corresponding hole on the carrier tool. This tool was subsequently moved to the cartridge and lowered on the cytometer cuvette. Pins on the tool were then able to engage corresponding holes on the cuvette and pick it up. The cuvette was transferred to a loading station elsewhere in the device.

Next, inside the device, a larger nozzle of the pipette was lowered into the cartridge to engage a pipette tip stored in the cartridge. The pipette and tip together were then used to mix the cells and plasma in the capped vessel by positioning the pipette tip within the sample in the capped vessel and repeatedly aspirating material into and dispensing material from the tip. Once the cells were resuspended in the plasma so that the whole blood sample was thoroughly mixed, 5 microliters of the mixed whole blood was aspirated to provide an aliquot for measurements of properties of the blood sample. This 5 microliter aliquot was used for measurements directed to the red blood cells and platelets in the sample. As discussed below, a portion of the sample remaining after removal of this 5 microliter aliquot was used for measurements directed at white blood cells in the sample.

The 5 microliters of whole blood was dispensed into a vessel containing a mixture of phosphate buffered saline and 2% by weight of bovine serum albumin, to dilute the whole blood twenty-fold (resulting in 100 microliters of diluted sample). After mixing vigorously, 5 microliters of this sample was transferred to another vessel containing a cocktail of labeling antibody reagents: anti-CD235a conjugated to alexa-fluor 647 (AF647), anti-CD41 and anti-CD61 conjugated to phycoerythrin (PE). The mixture was incubated for 5 minutes. Subsequently, 10 microliters of this mixture was mixed with 90 microliters of a buffer containing a zwitterionic surfactant at <0.1% by weight. The surfactant molecules modify bending properties of the red cell membrane such that all cells assume a stable spherical shape. This transformation is isovolumetric as the buffer used is isotonic with cytoplasm and no exchange of fluid can occur across the cell membrane. After incubating this for another 2 minutes, 30 microliters of this solution was mixed with a solution containing glutaraldehyde, a fixative and non-fluorescent beads of 10 um diameter. The mixture had a final concentration of 0.1% glutaraldehyde and 1000 beads per microliter. Glutaraldehyde rapidly fixes cells thus preventing cell lysis and other active biological processes.

The pipette then engaged a tip in the cartridge, aspirated 7 microliters of the above mixture of and loaded the 7 microliters into a channel within the cuvette placed on a platform with the carrier tool. After the mixture was loaded in into cuvette, the pipette aspirated 10 microliters of mineral oil from a vessel in the cartridge, and placed a drop of mineral oil on both open ends of the loaded channel of the cuvette. Mineral oil was added to the ends of the open channel to prevent evaporation of liquid from the loaded cuvette channel. Next, the device-level sample handling apparatus engaged the cuvette carrier/cuvette combination, and transported the cuvette carrier/cuvette combination from the module containing the cartridge to the cytometry module of the device. At the cytometry module, the device-level sample handling apparatus placed the cuvette carrier/cuvette combination on the microscopy stage of the cytometry module. The time required for these operations, in addition to a 2 minute wait time allowed the swollen cells to settle to the floor of the cuvette prior to imaging.

After the cuvette carrier/cuvette was placed on the microscopy stage, the stage was moved to pre-determined location so that the optical system of the cytometer could view one end of the channel containing the sample. At this location, the optical system relayed images of the sample acquired with darkfield illumination from a ringlight. These images coupled with actuation of the optical system on an axis perpendicular to the plane of the cuvette were used to find the plane of best focus. Once focused, the optical system was used to acquire fluorescence images of the sample at different wavelengths, commensurate with the fluorophores that were being used. For example, to visualize red blood cells that had been labeled with anti-CD235 conjugated to alexa fluor 647, a red (630 nm wavelength) light source was used to excite the sample and wavelengths between 650 nm and 700 nm were used to image the sample. A combination of a polychroic mirror and a bandpass emission filter was used to filter out unwanted wavelengths from the optical signal. Since the cells had settled on the floor of the cuvette, images at a single plane of focus were sufficient to visualize all cells in the region.

Data from the images was processed by a controller associated with the sample processing device. The image processing algorithms employed here utilized fluorescence images of cells to detect them using a combination of adaptive thresholding and edge detection. Based on local intensity and intensity gradients, regions of interest (RoI) were created around each cell. Using darkfield images, beads in the sample were also identified and RoIs were created around the beads. All the RoIs in each field of view were enumerated and their intensity in each image of that field of view were calculated. The information output by the image processing algorithm consisted of shape or morphometric measurements and fluorescence and darkfield intensities for each RoI. This information was analyzed using statistical methods to classify each object as either a red blood cell (positive for CD235a, but negative for CD41/CD61), a platelet (positive for CD41/CD61 and negative CD235a) or a bead. The shape descriptors such as perimeter, diameter and circularity were used to calculate the volume of each red blood cell and platelet. Since the beads were added at a known concentration, the average ratio of beads to cells over the whole channel was used to calculate cell concentration in terms of cells/microliter. Based on the steps performed for processing the sample, this concentration was corrected for dilution to arrive at concentration of cells in the original whole blood sample. The following quantities were calculated from a sample: 1) number of red blood cells in the cuvette; 2) average volume of red blood cells in the cuvette; 3) red blood cell distribution width (RDW) of red blood cells in the cuvette; 4) number of platelets in the cuvette; and 5) average volume of platelets in the cuvette. Based on these calculations, the following was calculated for the original blood sample.

| Measured Value | Result | Exemplary Range |
|---|---|---|
| Concentration of red blood cells (million cells per microliter) | 4.8 | 4-6 |
| Mean volume of red blood cells, femtoliter | 88 | 80-100 |
| red blood cell distribution width (RDW), (%) | 12 | 11-14.6 |
| Concentration of platelets (thousand cells per microliter) | 254 | 150-400 |
| Mean volume of platelets, femtoliter | 10.4 | 7.5-11.5 |

After removal of the 5 microliter aliquot used for analysis of RBC and platelet information, the remaining 75 microliters of sample was used to analyze the white blood cell population of the whole blood sample. The remaining 75 microliters of whole blood had also been mixed by repeatedly aspirating and dispensing the sample within the same the vessel by the pipette. Approximately 40 microliters of the remaining 75 microliters of mixed whole blood was aspirated into a pipette tip, and transferred by the pipette to a centrifuge tube in the cartridge. The centrifuge tube containing the blood sample was engaged by the pipette, and transferred to and deposited in a swinging bucket in a centrifuge within the module. The centrifuge was spun to provide 1200×g for 3 minutes, separating the blood into EDTA-containing plasma as the supernatant and packed cells in the pellet.

After centrifugation, the centrifuge tube was removed from the centrifuge and returned to the cartridge. The plasma supernatant was removed by the pipette and transferred to a separate reaction vessel in the cartridge. From a reagent vessel in the cartridge, 16 microliters of resuspension buffer was aspirated by the pipette, and added to the cell pellet in the centrifuge tube. The pipette then resuspended the cell pellet in the resuspension buffer by repeatedly aspirating and dispensing the mixture in the centrifuge tube. Next, the pipette aspirated 21 microliters of the resuspended whole blood and added it to another vessel containing 2 microliters of anti CD14-pacific blue and DRAQ5®, mixed, and incubated for 2 minutes. Twenty microliters of this mixture was then added to 80 microliters of a lysis buffer. The lysis buffer is a solution of a gentle surfactant such a saponin in conjunction with a fixative such as paraformaldehyde. The detergent causes a large number of holes to be formed in the membranes of cells. Red blood cells, due to their unique membrane properties, are particularly susceptible to this hole formation and lyse completely, their contents leaking out into the liquid around. Presence of the fixative prevents unintentional lysis of the white blood cells. Platelets also remain unlysed. The purpose of this step is to remove red blood cells from the mixture as they outnumber white blood cells by about 1000:1. Platelets do not interfere with imaging and hence are irrelevant to this process. The lysis buffer also contained 10 µM non-fluorescent beads at a known concentration.

After a 5 minute incubation, the vessel was spun again at 1200×g for 3 minutes. The supernatant was aspirated by a pipette tip, removing the red blood cell ghosts and other debris, and deposited into a waste area in the cartridge. Approximately 15 microliters of liquid with packed white blood cells were present in the cell pellet.

In order to determine a rough approximation of the number of white blood cells present in the cell pellet, the pipette first resuspended the white blood cells in the vessel and then aspirated the liquid, transferred it to spectrophotometer in the blade The white blood cell suspension was illuminated with light at a wavelength of 632 nm, which is the excitation wavelength for alexa fluor 647 dye and DRAQ5®. The light emitted by the cell suspension was filtered by a 650 nm long pass filter and measured in the spectrophotometer. This measurement was correlated with previously generated calibration curve to estimate a rough concentration of white blood cells in the cell suspension. Typically, cell concentrations ranged from about 1000 cells per microliter to about 100,000 cells per microliter. This estimate was used to calculate an appropriate dilution factor to ensure that the concentration of cells in the cuvette was constrained to within a two-fold range around a pre-defined target concentration. The purpose of this step was to ensure that cells are not present at too high or too low a density on the cuvette. If the cell density is too high, the accuracy of image processing algorithms is compromised, and if the cell density is too low, an insufficient number of cells are sampled.

Based on the dilution factor calculated in the above step, a diluent containing labeled antibodies against CD45 (pan-leukocyte marker), CD16 (neutrophil marker) and CD123 (basophil marker) was added to the cell suspension and mixed.

Once the cuvette in complex with cuvette carrier was placed on the cuvette carrier block, 10 microliters of the mixture of white blood cells resuspended in cytometry buffer was loaded into each of two channels in the cuvette. After the mixture was loaded into channels of the cuvette, the pipette aspirated 10 µl of mineral oil from a vessel in the cartridge, and placed a drop of mineral oil on both open ends of both channels in the cuvette loaded with white blood cells.

Next, the device-level sample handling apparatus engaged the cuvette carrier/cuvette combination, and transported the cuvette carrier/cuvette combination from the module containing the cartridge to the cytometry module of the device. At the cytometry module, the device-level sample handling apparatus placed the cuvette carrier/cuvette combination on the microscopy stage of the cytometry module. After the cuvette carrier/cuvette was placed on the microscopy stage, the two channels of the cuvette containing white blood cells were imaged as described above for the RBC/platelet mixture.

Darkfield images of the white blood cells were used to count the numbers of cells in a field (as shown in FIG. 1A). Cell surface markers were used to determine the cell type of individual white blood cells in an image; for example, CD14 marks monocytes; CD123 marks basophils; CD16 marks neutrophils; and CD45-AF647 were used to mark all leukocytes (FIGS. 1B-1E). The nuclear stain DRAQ5® was used to mark cell nuclei, and so to differentiate nucleate cells (such as white blood cells) from mature red blood cells, which have no nucleus.

The image processing algorithms employed here utilized fluorescence images of cells to detect them using a combination of adaptive thresholding and edge detection. Based on local intensity and intensity gradients, boundaries of regions of interest (RoI) were created around each cell. Using darkfield images, beads in the sample were also identified and RoI boundaries were created around the beads. All the RoIs in each field of view were enumerated and their intensity in each image of that field of view were calculated. The information output by the image processing algorithm consisted of shape or morphometric measurements and fluorescence and darkfield intensities for each RoI. This information was analyzed using statistical methods to classify each object as a lymphocyte, monocyte, basophil, eosinophil, neutrophil or a bead. Based on enumeration of cells of different types, the corresponding bead count and the dilution ratio implemented during sample processing, an absolute concentration of cells per microliter of original whole blood was calculated. This was calculated for all white blood cells and each subtype, and reported as both absolute concentration (cells per microliter) and proportion (%).

Figure 2:
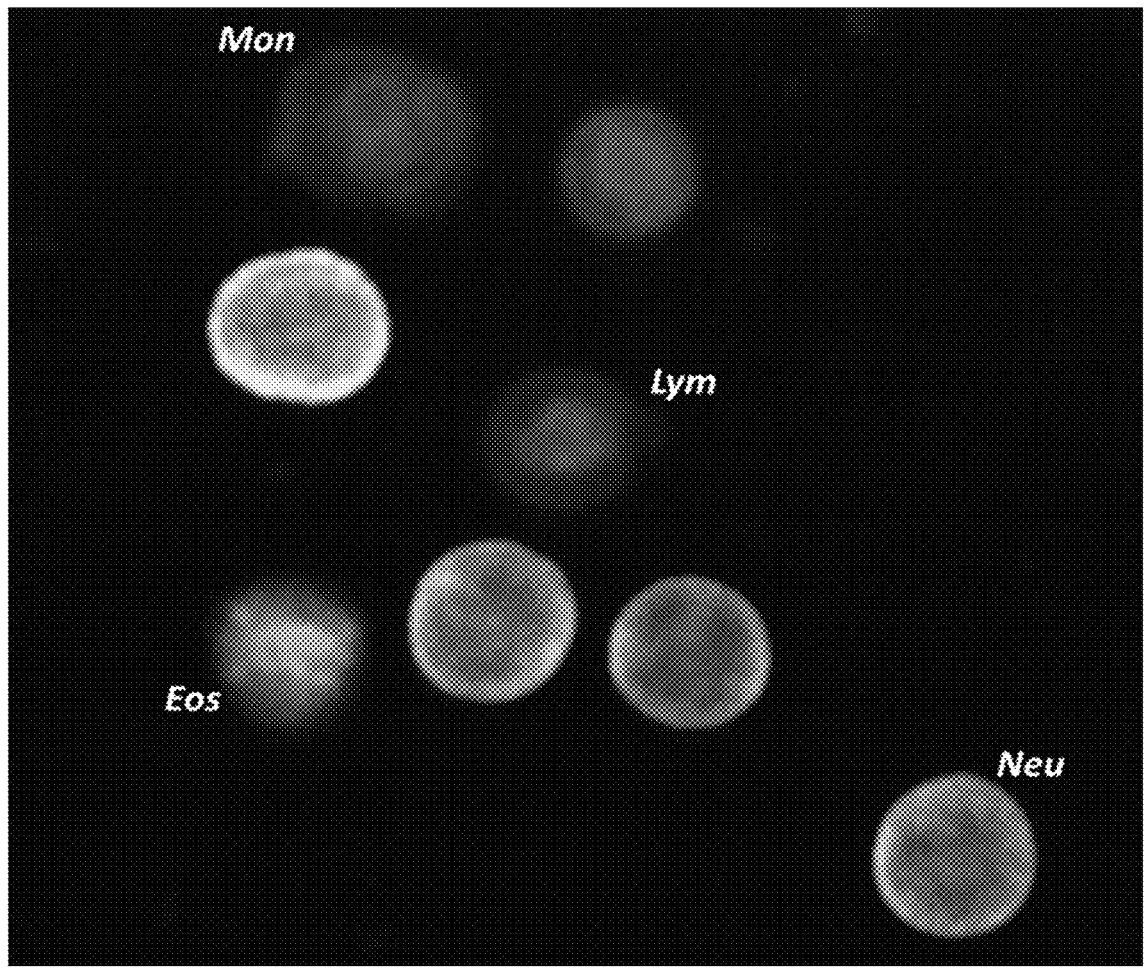
FIG. 2 shows a representative composite image of several cell-types in whole blood, including images of a monocyte, a lymphocyte, an eosinophil, and a neutrophil.
Figure 3:
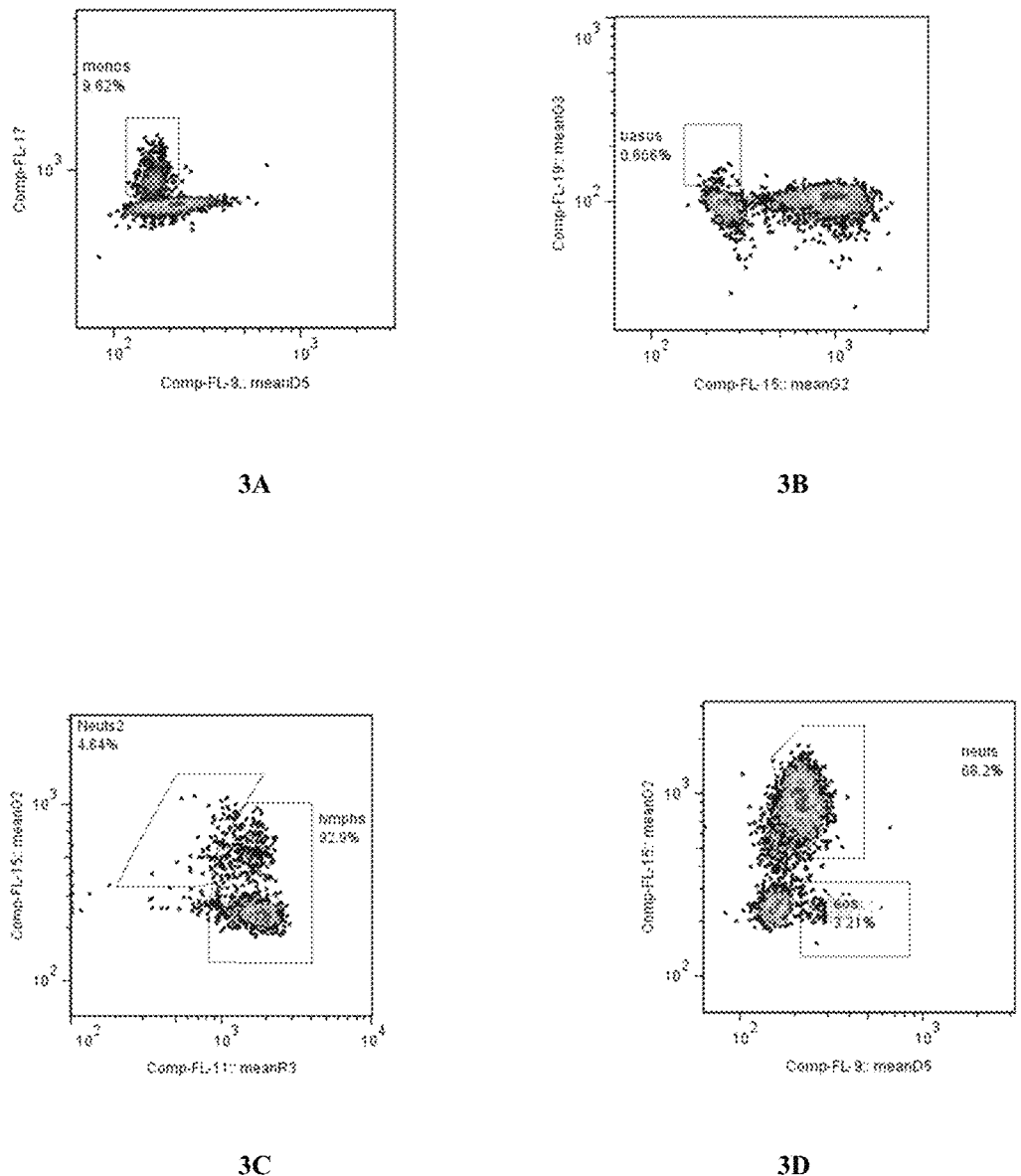
FIG. 3A shows plots of monocytes identified and quantified by the cytometric assays described herein.
FIG. 3B shows plots of basophils identified and quantified by the cytometric assays described herein.
FIG. 3C shows plots of lymphocytes identified and quantified by the cytometric assays described herein.
FIG. 3D shows plots of neutrophils and eosinophils identified and quantified by the cytometric assays described herein.

Examples of images and plots of results of such measurements are presented in FIGS. 1, 2, and 3.

FIG. 1 shows representative images of blood cells from a sample of whole blood; these images were taken using different imaging techniques and dyes. The image shown in FIG. 1A was taken of cells from whole blood using darkfield illumination. The image shown in FIG. 1B was taken of cells from whole blood showing fluorescence from anti-CD14 antibodies labeled with PAC Blue dye; the fluorescent cells are monocytes. The image shown in FIG. 1C was taken of cells from whole blood showing fluorescence from anti-CD123 antibodies labeled with PECy5 dye; the fluorescent cells are basophils. The image shown in FIG. 1D was taken of cells from whole blood showing fluorescence from anti-CD16 antibodies labeled with PE dye; the fluorescent cells are neutrophils. The image shown in FIG. 1E was taken of cells from whole blood showing fluorescence from anti-CD45 antibodies labeled with AF647 dye; all leukocytes fluoresce under these conditions. The image shown in FIG. 1F was taken of cells from whole blood dyed with DRAQ5® to stain cell nuclei. Thus, leukocytes and platelets are stained and fluoresce under these conditions, but red blood cells (lacking nuclei) are not stained and do not fluoresce.

FIG. 2 shows a representative composite image of cell-types in whole blood from images acquired according to the methods disclosed herein. Images of a monocyte (labeled and seen in the upper left quadrant of the figure, with a reddish center surrounded by a blue-purple ring), a lymphocyte (labeled and seen in the center of the figure, with a bright red center surrounded by a dimmer red ring), an eosinophil (labeled and seen in the lower left quadrant of the figure, with a green center surrounded by a red border), and a neutrophil (labeled and seen in the lower right quadrant of the figure, with a green center surrounded by a yellow and green border) are shown in the figure.

It is of interest to identify and quantify various cell types found in such blood samples. There may be multiple ways to approach such a classification process, which, in some embodiments, may be considered as being a statistical problem for multi-dimensional classification. It will be understood that a wide variety of methods are available in the field to solve these types of classification problems. A particular embodiment of such an analysis is provided below.

FIG. 3 shows plots of various cell types identified and quantified by the cytometric assays described in this example. FIG. 3A shows a plot of spots (cells) by intensity of the marker FL-17 versus intensity of the marker FL-9 to identify monocytes. FIG. 3B shows a plot of spots (cells) by intensity of the marker FL-19 versus intensity of the marker FL-15 to identify basophils. FIG. 3C shows a plot of spots (cells) by intensity of the marker FL-15 versus intensity of the marker FL-11 to identify lymphocytes. FIG. 3D shows a plot of spots (cells) by intensity of the marker FL-15 versus intensity of the marker FL-9 to identify neutrophils and eosinophils.

The initial identification of monocytes (9.6%, as shown in FIG. 3A) is used to guide the subsequent identification of basophils (0.68%, as shown in FIG. 3B). The identification of monocytes and basophils as shown in FIGS. 3A and 3B is used to guide the subsequent identification of neutrophils and eosinophils (68% neutrophils, 3.2% eosinophils, of the WBCs shown in FIG. 3D). Finally, lymphocytes are identified as shown in FIG. 3C (93% of the WBCs plotted in FIG. 3D, corresponding to 18% of the cells in the original sample).

Figure 4:
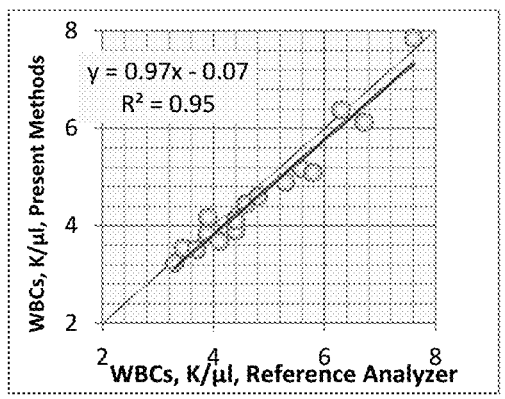
FIG. 4A shows plots of numbers of white blood cells ("WBCs") demonstrating that cytometric methods as disclosed herein identify different cell types consistent with such identification by other methods.
FIG. 4B shows plots numbers of red blood cells ("RBCs) demonstrating that cytometric methods as disclosed herein identify different cell types consistent with such identification by other methods.
FIG. 4C shows plots numbers of platelets demonstrating that cytometric methods as disclosed herein identify different cell types consistent with such identification by other methods.
FIG. 4D shows plots numbers of monocytes demonstrating that cytometric methods as disclosed herein identify different cell types consistent with such identification by other methods.
FIG. 4E shows plots numbers of lymphocytes demonstrating that cytometric methods as disclosed herein identify different cell types consistent with such identification by other methods.
FIG. 4F shows plots of numbers of lymphocytes.
Figure 4:
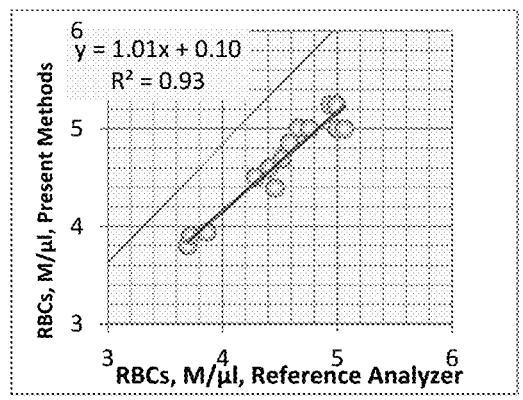
Figure 4:
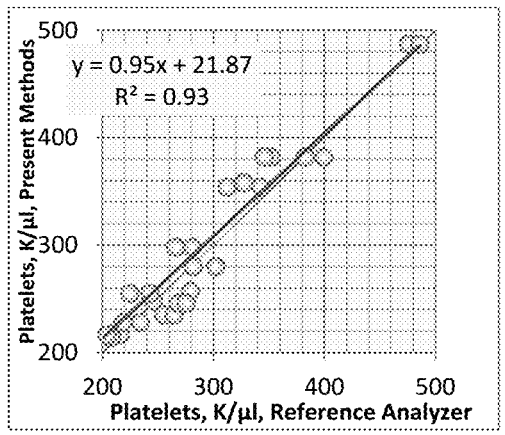
Figure 4:
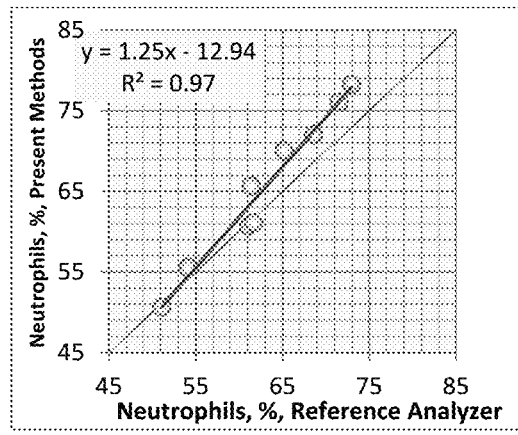
Figure 4:
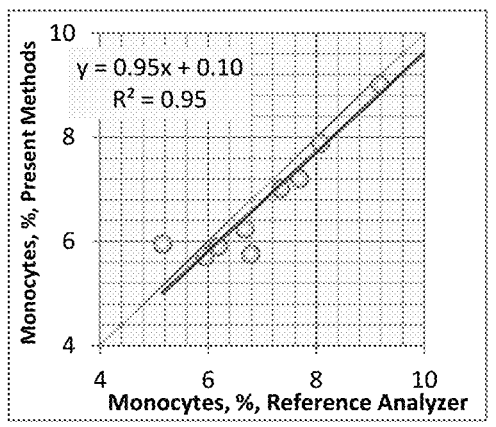
Figure 4:
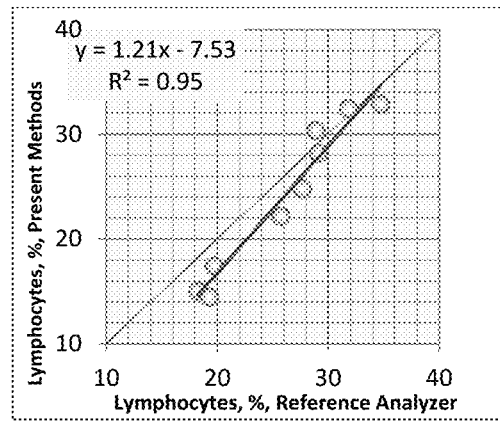

The present methods correlate well with other methods. Counts of white blood cells, red blood cells, and platelets were made with samples of EDTA-anti coagulated whole blood. The white blood cells were further counted to determine the numbers of neutrophils, monocytes, and lymphocytes in the sample. In the measurements shown in FIG. 9, EDTA-anti coagulated whole blood samples were split into two, and one part of the samples were run on the system disclosed herein, using the methods disclosed herein. The other part of the samples was run on an Abbott CELL-DYN Ruby System (Abbott Diagnostics, Lake Forest, Ill., USA), a commercial multi-parameter automated hematology analyzer. A comparison of the results obtained with both methods is shown in FIG. 4.

As shown in FIGS. 4A-4C, the numbers of white blood cells ("WBCs", FIG. 4A), red blood cells ("RBCs", FIG. 4B) and platelets (FIG. 4C) measured by the present methods correlate well with the numbers of WBCs, RBCs, and platelets measured by other methods in corresponding aliquots of the same samples as were analyzed by the present methods. As shown in FIGS. 4D-4F, the numbers of neutrophils, monocytes, and lymphocytes measured by either method were very similar, and correlated well with each other.

While the above is a complete description of the preferred embodiment as described herein, it is possible to use various alternatives, modifications and equivalents. Therefore, the scope of the present invention should be determined not with reference to the above description but should, instead, be determined with reference to the appended claims, along with their full scope of equivalents. Any feature, whether preferred or not, may be combined with any other feature, whether preferred or not. The appended claims are not to be interpreted as including means-plus-function limitations, unless such a limitation is explicitly recited in a given claim using the phrase "means for." It should be understood that as used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise. Finally, as used in the description herein and throughout the claims that follow, the meanings of "and" and "or" include both the conjunctive and disjunctive and may be used interchangeably unless the context expressly dictates otherwise. Thus, in contexts where the terms "and" or "or" are used, usage of such conjunctions do not exclude an "and/or" meaning unless the context expressly dictates otherwise.

This document contains material subject to copyright protection. The copyright owner (Applicant herein) has no objection to the facsimile reproduction by anyone of the patent document or the patent disclosure, as they appear in the US Patent and Trademark Office patent file or records, but otherwise reserves all copyright rights whatsoever. The following notice shall apply: Copyright 2013-2014 Theranos, Inc.

The invention claimed is:

1. A method of testing a biological sample in an automated assay device, comprising:
   providing the automated assay device;
   providing a cartridge with the biological sample to the automated assay device;
   dividing the biological sample into a plurality of portions and retaining a portion of the biological sample in a separate storage container in said automated assay device;
   performing an initial assay in said automated assay device for an analyte in said biological sample, whereby an initial result is obtained, wherein said initial assay may provide a negative result indicating that a presence of said analyte is not detected, or is detected at a level within a predetermined range in the biological sample, in the biological sample, or may provide a positive result indicating that the presence of the analyte is detected in the biological sample;
   reviewing said initial result; and
   determining further testing of said biological sample contingent on said initial result, wherein if the initial result is negative, then no further assay is performed on said biological sample; and wherein if the initial result is positive, then a further assay is performed in said automated assay device on said portion of the biological sample from the separate storage container in said automated assay device, wherein the further assay is performed only after said initial result is reviewed wherein said portion upon which the further assay is performed is obtained before the result of the initial assay is obtained, and said retained portion is retain in reserve in said automated assay device, wherein the cartridge is pre-loaded with reagents required by the initial assay, and also pre-loaded with reagents used for said further assay.

2. The method of claim 1, wherein said further assay comprises an assay of a type selected from a group of assay types consisting of antibody-based assays, nucleic acid assays, general chemistry assays, and cytometric assays.

3. The method of claim 1, wherein said further assay comprises a different type of assay than said initial assay.

4. The method of claim 1, wherein the analyte to be detected by said further assay comprises a different analyte than the analyte detected by said initial assay.

5. The method of claim 1, wherein the initial assay comprises measurement of an analyte, and said further assay comprises a cytometric assay.

6. The method of claim 5, wherein said cytometric assay comprises a measurement of a morphological characteristic of a blood cell in a blood sample.

7. The method of claim 1, wherein said initial assay comprises use of a detector to obtain said initial result, wherein said detector is selected from an optical detector, a pH detector, an electrochemical detector, a temperature sensor, an ion-sensitive electrode, a radiation detector, and other detectors.

8. The method of claim 1, wherein said further assay comprises a use of a detector to obtain a further result, wherein said detector is selected from an optical detector, a pH detector, an electrochemical detector, a temperature sensor, an ion-sensitive electrode, a radiation detector, and other detectors.

9. The method of claim 1, wherein said further assay comprises an assay that is more sensitive for the detection of said analyte than said initial assay.

10. The method of claim 1, wherein said biological sample comprises a sample selected from blood, serum, plasma, a throat swab sample, a nasal swab sample, a nasopharyngeal wash sample, saliva, urine, gastric fluid, cerebrospinal fluid, tears, stool, mucus, sweat, earwax, oil, a glandular secretion, semen, vaginal fluid, interstitial fluids derived from tumorous tissue, ocular fluids, breath, hair, finger nails, skin, biopsy tissue, placental fluid, amniotic fluid, cord blood, lymphatic fluids, cavity fluids, sputum, pus, microbiota, meconium, breast milk, and other secretions or excretions.

11. The method of claim 1, wherein said initial assay and said further assay are performed on different portions of a single biological sample.

12. The method of claim 11, wherein at least one of said different portions of said single biological sample comprises a diluted biological sample.

13. A method of testing a biological sample in a sample processing device, comprising:
   providing the sample processing device;
   providing a cartridge with the biological sample to the sample processing device;
   performing an initial assay in said sample processing device for an analyte in said biological sample, whereby an initial result is obtained, wherein said initial assay may provide a negative result indicating that a presence of said analyte is not detected, or is detected at a level within a predetermined range, in the biological sample, or may provide a positive result indicating that the presence of the analyte is detected in the biological sample; and determining further testing contingent on said initial result, wherein if the initial result is negative, then no further assay is performed; and wherein if the initial result is positive, then a further assay is performed in said sample processing device, wherein said further assay is performed on a separate biological sample, wherein said separate biological sample is provided in said sample processing device to perform said further assay, wherein said separate biological sample upon which the further assay is performed is obtained before a result of the initial assay is obtained, and said separate biological sample is stored in said sample processing device, wherein the cartridge is pre-loaded with reagents required by the initial assay, and also pre-loaded with reagents used for said further assay.

14. The method of claim 13, wherein said biological sample and said separate biological sample are each of a same type of sample.

15. The method of claim 14, wherein said biological sample and said separate biological sample are each a blood sample.

16. The method of claim 15, wherein said biological sample and said separate biological sample are each a different fraction of blood.

17. The method of claim 16, wherein said fractions of blood are selected from whole blood, serum, and plasma.

18. The method of claim 13, wherein said biological sample and said separate biological sample are each different types of biological samples.

19. The method of claim 18, wherein said different types of biological samples are selected from the group of biological sample types consisting of blood, serum, plasma, a throat swab sample, a nasal swab sample, a nasopharyngeal wash sample, saliva, urine, gastric fluid, cerebrospinal fluid, tears, stool, mucus, sweat, earwax, oil, a glandular secretion, semen, vaginal fluid, interstitial fluids derived from tumorous tissue, ocular fluids, breath, hair, finger nails, skin, biopsy tissue, placental fluid, amniotic fluid, cord blood, lymphatic fluids, cavity fluids, sputum, pus, microbiota, meconium, breast milk, and other secretions or excretions.

* * * * *